United States Patent
Butt et al.

(10) Patent No.: US 10,988,785 B1
(45) Date of Patent: Apr. 27, 2021

(54) ISOLATED CODON SEQUENCE

(71) Applicant: CB Therapeutics, INC., Carlsbad, CA (US)

(72) Inventors: Sher Ali Butt, San Diego, CA (US); Jacob Michael Vogan, San Diego, CA (US)

(73) Assignee: CB THERAPEUTICS, INC., Carlsbad, CA (US)

( * ) Notice: Subject to any disclaimer, the term of this patent is extended or adjusted under 35 U.S.C. 154(b) by 0 days.

(21) Appl. No.: 16/553,120

(22) Filed: Aug. 27, 2019

Related U.S. Application Data

(60) Division of application No. 15/719,430, filed on Sep. 28, 2017, now Pat. No. 10,435,727, which is a continuation of application No. 15/096,164, filed on Apr. 11, 2016, now abandoned.

(60) Provisional application No. 62/145,430, filed on Apr. 9, 2015.

(51) Int. Cl.
| | |
|---|---|
| C12P 17/06 | (2006.01) |
| C12P 13/02 | (2006.01) |
| C12P 7/42 | (2006.01) |
| C12N 15/52 | (2006.01) |
| C12P 7/22 | (2006.01) |

(52) U.S. Cl.
CPC .............. *C12P 13/02* (2013.01); *C12N 15/52* (2013.01); *C12P 7/22* (2013.01); *C12P 7/42* (2013.01); *C12P 17/06* (2013.01)

(58) Field of Classification Search
None
See application file for complete search history.

(56) References Cited

U.S. PATENT DOCUMENTS

| | | | |
|---|---|---|---|
| 6,630,507 | B1 | 10/2003 | Hampson |
| 7,179,800 | B2 | 2/2007 | Martin |
| 8,884,100 | B2 | 11/2014 | Page |
| 9,394,510 | B2 | 7/2016 | Peet |
| 9,822,384 | B2 | 11/2017 | Poulos |
| 2007/0032544 | A1 | 2/2007 | Korthout |
| 2008/0031977 | A1 | 2/2008 | Musty |
| 2009/0042964 | A1 | 2/2009 | Malamas |
| 2009/0042974 | A1 | 2/2009 | Parker |
| 2010/0016418 | A1 | 1/2010 | Guy |
| 2010/0292345 | A1 | 11/2010 | Pertwee |
| 2011/0021617 | A1 | 1/2011 | Korthout |
| 2011/0098348 | A1 | 4/2011 | DeMeijer |
| 2012/0144523 | A1 | 6/2012 | Page |
| 2015/0128301 | A1 | 5/2015 | Page |
| 2016/0010126 | A1 | 1/2016 | Poulos |

FOREIGN PATENT DOCUMENTS

| | | |
|---|---|---|
| WO | WO2011017798 A1 | 2/2011 |
| WO | WO2016010827 A1 | 1/2016 |

OTHER PUBLICATIONS

Tang et al. (Nucleic Acids Research, 1994, vol. 22, No. 14 2857-2858).*

Taura, F Studies on tetrahydrocannabinolic acid synthase that produces the acidic precursor of tetrahydrocannabinol, the pharmacologically active cannabinoid in marijuana. Drug Discov Ther. 2009; 3(3):83-87.

Taura, F. et al. Purification and Characterization of Cannabidiolic-acid Synthase from *Cannabis sativa* L.:. Biochemical Analysis of a Novel Enzyme That Catalyzes the Oxidocyclization of Cannabigerolic Acid to Cannabidiolic Acid. J. Biol. Chem. 1996; 271: 17411-17416.

Taura. F et al. Cannabidiolic-acid synthase, the chemotype-determining enzyme in the fiber-type Cannabis sativa. FEBS Letters. 2007; 581: 2929-2934.

Fellermeier M. et al. Biosynthesis of cannabinoids: Incorporation experiments with 13C-labeled glucose. Eur. J. Biochem. 2008; 268: 1596-1064.

Fellermeier, M. et al. Prenylation of olivetolate by a hemp transferase yields cannabigerolic acid, the precursor of tetrahydrocannabinol. FEBS Letters. 1998; 427: 283-285.

Nevoigt, E. Progress in metabolic engineering of *Saccharomyces cerevisiae*. Microbiology and Molecule Biology Reviews. 2009; 72: 378-412.

Flores-Sanchez, U. et al. Secondary metabolism in cannabis. Phytochem Rev. 2008; 7: 615-639.

Eisenreich, W. et al. The deoxyxylulose phosphate pathway of terpenoid biosynthesis in plants and microorganisms. Chemistry & Biology. 1998; 5: R221-R233.

Gagne, S.J. et al. Identification of olivetolic acid from Cannabis sativa reveals a unique catalytic route to plant polyketides, PNAS, 2012, 109: 12811-12816.

* cited by examiner

*Primary Examiner* — Hope A Robinson
(74) *Attorney, Agent, or Firm* — Torrey Pines Law Group, PC

(57) ABSTRACT

The present invention is a method for the biosynthesis of hundreds of compounds, mainly found in the *cannabis* plant. The starting material for these compounds can be any biological compound that is used/produced in a biological organism from the sugar family starting materials or other low cost raw materials processed via enzymes or within organisms to give final products. These final products include, but are not limited to: cannabinoids, terpenoids, stilbenoids, flavonoids, phenolic amides, lignanamides, spermidine alkaloids, and phenylpropanoids. Specifically, the present invention relates to the regular, modified, or synthetic gene(s) of select enzymes that are processed and inserted into an expression system (for example, a vector, cosmid, BAC, YAC, phage) to produce modified hosts. The modified host is then optimized for efficient production and yield via manipulation, silencing, and amplifying inserted or other genes in the host, leading to an efficient system for product.

4 Claims, 8 Drawing Sheets

Specification includes a Sequence Listing.

(Genetic Modifications of Genes in our Pathway for Accelerated High Yield Development)

MVA Pathway

Alternative HMG-CoA Pathway for Leucine Catabolism

SEQUENCE LISTING

<160> NUMBER OF SEQ ID NOS: 36

<210> SEQ ID NO 1
<211> LENGTH: 60
<212> TYPE: DNA
<213> ORGANISM: Artificial Sequence
<220> FEATURE:
<223> OTHER INFORMATION: Synthetic: ERG9pS1

<400> SEQUENCE: 1
gtacatttca tagcccatct tcaacaacaa taccgactta cccgtacgct gcaggtcgac    60

<210> SEQ ID NO 2
<211> LENGTH: 60
<212> TYPE: DNA
<213> ORGANISM: Artificial Sequence
<220> FEATURE:
<223> OTHER INFORMATION: Synthetic: ERG9 250dwS2

<400> SEQUENCE: 2
cagattgacg gagagagggc cacattgttt gtcggcaata aatcgatgaa ttcgagctcg    60

<210> SEQ ID NO 3
<211> LENGTH: 22
<212> TYPE: DNA
<213> ORGANISM: Artificial Sequence
<220> FEATURE:
<223> OTHER INFORMATION: Synthetic: Hph F

<400> SEQUENCE: 3
atgggtaaaa agcctgaact ca                                              22

<210> SEQ ID NO 4
<211> LENGTH: 23
<212> TYPE: DNA
<213> ORGANISM: Artificial Sequence
<220> FEATURE:
<223> OTHER INFORMATION: Synthetic: Hph R

<400> SEQUENCE: 4
ttattccttt gccctcggac gag                                             23

<210> SEQ ID NO 5
<211> LENGTH: 22
<212> TYPE: DNA
<213> ORGANISM: Artificial Sequence
<220> FEATURE:
<223> OTHER INFORMATION: Synthetic: ERG9 450dwR

<400> SEQUENCE: 5
agatgctagt caatggcaga ag                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic: ERG9p300upF

<400> SEQUENCE: 6
tgcttacaca gagtgaacct gc                                              22

<210> SEQ ID NO 7
<211> LENGTH: 19
<212> TYPE: DNA
<213> ORGANISM: Artificial Sequence

```
<220> FEATURE:
<223> OTHER INFORMATION: Synthetic: ERG9 300R

<400> SEQUENCE: 7
ctcgtggaag tgacgcaac                                                19

<210> SEQ ID NO 8
<211> LENGTH: 32
<212> TYPE: DNA
<213> ORGANISM: Artificial Sequence
<220> FEATURE:
<223> OTHER INFORMATION: Synthetic: pGPD-BamHI F

<400> SEQUENCE: 8
cgggatccag tttatcatta tcaatactcg cc                                 32

<210> SEQ ID NO 9
<211> LENGTH: 31
<212> TYPE: DNA
<213> ORGANISM: Artificial Sequence
<220> FEATURE:
<223> OTHER INFORMATION: Synthetic: pGPD-NotIR

<400> SEQUENCE: 9
ggggcggccg cgagctcagt ttatcattat c                                  31

<210> SEQ ID NO 10
<211> LENGTH: 42
<212> TYPE: DNA
<213> ORGANISM: Artificial Sequence
<220> FEATURE:
<223> OTHER INFORMATION: Synthetic: tHMGR-NotIF

<400> SEQUENCE: 10
ggggcggccg caaaacaatg ttgtcacgac ttttccgtat gc                      42

<210> SEQ ID NO 11
<211> LENGTH: 37
<212> TYPE: DNA
<213> ORGANISM: Artificial Sequence
<220> FEATURE:
<223> OTHER INFORMATION: Synthetic: tHMGR-SpeIR

<400> SEQUENCE: 11
gactagttca agctgacttc ttggtgcacg ttccttg                            37

<210> SEQ ID NO 12
<211> LENGTH: 25
<212> TYPE: DNA
<213> ORGANISM: Artificial Sequence
<220> FEATURE:
<223> OTHER INFORMATION: Synthetic: ERG1F

<400> SEQUENCE: 12
atgtctgctg ttaacgttgc acctg                                         25

<210> SEQ ID NO 13
<211> LENGTH: 22
<212> TYPE: DNA
<213> ORGANISM: Artificial Sequence
<220> FEATURE:
<223> OTHER INFORMATION: Synthetic: ERG1R

<400> SEQUENCE: 13
ttaaccaatc aactcaccaa ac                                            22
```

<210> SEQ ID NO 14
<211> LENGTH: 38
<212> TYPE: DNA
<213> ORGANISM: Artificial Sequence
<220> FEATURE:
<223> OTHER INFORMATION: Synthetic: ERG1-split F

<400> SEQUENCE: 14
cgggatccct cgagttgttc gctgctgaca gcgataac                        38

<210> SEQ ID NO 15
<211> LENGTH: 44
<212> TYPE: DNA
<213> ORGANISM: Artificial Sequence
<220> FEATURE:
<223> OTHER INFORMATION: Synthetic: ERG1-splitR

<400> SEQUENCE: 15
cgggatccgc tagcggtacc acatgggtcc tttatattga cacg                 44

<210> SEQ ID NO 16
<211> LENGTH: 23
<212> TYPE: DNA
<213> ORGANISM: Artificial Sequence
<220> FEATURE:
<223> OTHER INFORMATION: Synthetic: ERG1 90up F

<400> SEQUENCE: 16
atcagaacaa ttgtccagta ttg                                        23

<210> SEQ ID NO 17
<211> LENGTH: 21
<212> TYPE: DNA
<213> ORGANISM: Artificial Sequence
<220> FEATURE:
<223> OTHER INFORMATION: Synthetic: ERG1100dwR

<400> SEQUENCE: 17
aatgtactat acaagccttc c                                          21

<210> SEQ ID NO 18
<211> LENGTH: 40
<212> TYPE: DNA
<213> ORGANISM: Artificial Sequence
<220> FEATURE:
<223> OTHER INFORMATION: Synthetic: bSQS-NotIF

<400> SEQUENCE: 18
ggggcggccg caaaacaatg gggatgcttc gctggggagt                      40

<210> SEQ ID NO 19
<211> LENGTH: 31
<212> TYPE: DNA
<213> ORGANISM: Artificial Sequence
<220> FEATURE:
<223> OTHER INFORMATION: Synthetic: bSQS-SpeIR

<400> SEQUENCE: 19
gactagttta gctcctcaat tcgtcaaagg t                               31

<210> SEQ ID NO 20
<211> LENGTH: 42
<212> TYPE: DNA
<213> ORGANISM: Artificial Sequence
<220> FEATURE:
<223> OTHER INFORMATION: Synthetic: Cre-NotIF

```
<400> SEQUENCE: 20
ggggcggccg caaaacaatg gacatgttca gggatcgcca gg                    42

<210> SEQ ID NO 21
<211> LENGTH: 31
<212> TYPE: DNA
<213> ORGANISM: Artificial Sequence
<220> FEATURE:
<223> OTHER INFORMATION: Synthetic: Cre-SpeIR

<400> SEQUENCE: 21
gactagtcta atcgccatct tccagcaggc g                                31

<210> SEQ ID NO 22
<211> LENGTH: 60
<212> TYPE: DNA
<213> ORGANISM: Artificial Sequence
<220> FEATURE:
<223> OTHER INFORMATION: Synthetic: Padh-Loxp-BamHIF

<400> SEQUENCE: 22
cgggatccat aacttcgtat agcatacatt atacgaagtt atgtggaata tttcggatat  60

<210> SEQ ID NO 23
<211> LENGTH: 56
<212> TYPE: DNA
<213> ORGANISM: Artificial Sequence
<220> FEATURE:
<223> OTHER INFORMATION: Synthetic: Padh-Kanmx4F

<400> SEQUENCE: 23
gcatacaatc aactaagcta agctaaaaca atgggtaagg aaaagactca cgtttc      56

<210> SEQ ID NO 24
<211> LENGTH: 56
<212> TYPE: DNA
<213> ORGANISM: Artificial Sequence
<220> FEATURE:
<223> OTHER INFORMATION: Synthetic: Padh-Kanmx4R

<400> SEQUENCE: 24
gaaacgtgag tcttttcctt acccattgtt ttagcttagc ttagttgatt gtatgc      56

<210> SEQ ID NO 25
<211> LENGTH: 53
<212> TYPE: DNA
<213> ORGANISM: Artificial Sequence
<220> FEATURE:
<223> OTHER INFORMATION: Synthetic: Kanmx4-TcycF

<400> SEQUENCE: 25
catttgatgc tcgatgagtt tttctaaatc cgctctaacc gaaaaggaag gag         53

<210> SEQ ID NO 26
<211> LENGTH: 53
<212> TYPE: DNA
<213> ORGANISM: Artificial Sequence
<220> FEATURE:
<223> OTHER INFORMATION: Synthetic: Kanmx4-TcycR

<400> SEQUENCE: 26
ctccttcctt ttcggttaga gcggatttag aaaaactcat cgagcatcaa atg         53

<210> SEQ ID NO 27
```

```
<211> LENGTH: 60
<212> TYPE: DNA
<213> ORGANISM: Artificial Sequence
<220> FEATURE:
<223> OTHER INFORMATION: Synthetic: Tcyc-LoxP-NheIR

<400> SEQUENCE: 27
ggggctagca taacttcgta taatgtatgc tatacgaagt tatcttcgag cgtcccaaaa        60

<210> SEQ ID NO 28
<211> LENGTH: 30
<212> TYPE: DNA
<213> ORGANISM: Artificial Sequence
<220> FEATURE:
<223> OTHER INFORMATION: Synthetic: Gpd-BamHIF

<400> SEQUENCE: 28
cgggatccag tttatcatta tcaatactcg                                         30

<210> SEQ ID NO 29
<211> LENGTH: 31
<212> TYPE: DNA
<213> ORGANISM: Artificial Sequence
<220> FEATURE:
<223> OTHER INFORMATION: Synthetic: Tadh-XhoIR

<400> SEQUENCE: 29
gggctcgagg agcgacctca tgctatacct g                                       31

<210> SEQ ID NO 30
<211> LENGTH: 22
<212> TYPE: DNA
<213> ORGANISM: Artificial Sequence
<220> FEATURE:
<223> OTHER INFORMATION: Synthetic: Kanmx4R

<400> SEQUENCE: 30
ttagaaaaac tcatcgagca tc                                                 22

<210> SEQ ID NO 31
<211> LENGTH: 55
<212> TYPE: DNA
<213> ORGANISM: Artificial Sequence
<220> FEATURE:
<223> OTHER INFORMATION: Synthetic: OLS 5' FWD

<400> SEQUENCE: 31
gcatagcaat ctaatctaag tttaaaatga atcatttgag agcagaaggg cctgc             55

<210> SEQ ID NO 32
<211> LENGTH: 56
<212> TYPE: DNA
<213> ORGANISM: Artificial Sequence
<220> FEATURE:
<223> OTHER INFORMATION: Synthetic: CB 5' FWD

<400> SEQUENCE: 32
caccagaact tagtttcgac ggataaaatg gaaaccggtt tgtcctcggt ttgcac            56

<210> SEQ ID NO 33
<211> LENGTH: 58
<212> TYPE: DNA
<213> ORGANISM: Artificial Sequence
<220> FEATURE:
<223> OTHER INFORMATION: Synthetic: All REV

<400> SEQUENCE: 33
```
cataactaat tacatgattt aaccttaaac atcagattca atagagccgc ctccactg    58

<210> SEQ ID NO 34
<211> LENGTH: 8873
<212> TYPE: DNA
<213> ORGANISM: Artificial Sequence
<220> FEATURE:
<223> OTHER INFORMATION: Synthetic

<400> SEQUENCE: 34
ggttaaatca tgtaattagt tatgtcacgc ttacattcac gccctccccc cacatccgct    60
ctaaccgaaa aggaaggagt tagacaacct gaagtctagg tccctattta ttttttata    120
gttatgttag tattaagaac gttatttata tttcaaattt ttcttttttt tctgtacaga    180
cgcgtgtacg catgtaacat tatactgaaa accttgcttg agaaggtttt gggacgctcg    240
aaggctttaa tttgcggccc ctcacctgca cgcaaaatag gataattata ctctatttct    300
caacaagtaa ttggttgttt ggccgagcgg tctaaggcgc ctgattcaag aaatatcttg    360
accgcagtta actgtgggaa tactcaggta tcgtaagatg caagagttcg aatctcttag    420
caaccattat ttttttcctc aacataacga gaacacacag gggcgctatc gcacagaatc    480
aaattcgatg actggaaatt ttttgttaat ttcagaggtc gcctgacgca tataccttt    540
tcaactgaaa aattgggaga aaaggaaag gtgagagcgc cggaaccggc ttttcatata    600
gaatagagaa gcgttcatga ctaaatgctt gcatcacaat acttgaagtt gacaatatta    660
tttaaggacc tattgttttt tccaataggt ggttagcaat cgtcttactt tctaactttt    720
cttaccttt acatttcagc aatatatata tatatatttc aaggatatac cattctaatg    780
tctgccccta gaagatcgt cgttttgcca ggtgaccacg ttggtcaaga atcacagcc    840
gaagccatta aggttcttaa agctatttct gatgttcgtt ccaatgtcaa gttcgatttc    900
gaaaatcatt taattggtgg tgctgctatc gatgctacag gtgttccact tccagatgag    960
gcgctggaag cctccaagaa ggctgatgcc gttttgttag gtgctgtggg tggtcctaaa    1020
tggggtaccg gtagtgttag acctgaacaa ggtttactaa aaatccgtaa agaacttcaa    1080
ttgtacgcca acttaagacc atgtaacttt gcatccgact ctcttttaga cttatctcca    1140
atcaagccac aatttgctaa aggtactgac ttcgttgttg tcagagaatt agtgggaggt    1200
atttactttg gtaagagaaa ggaagatgat ggtgatggtg tcgcttggga tagtgaacaa    1260
tacaccgttc cagaagtgca aagaatcaca agaatggccg ctttcatggc cctacaacat    1320
gagccaccat tgcctatttg gtccttggat aaagctaatg ttttggcctc ttcaagatta    1380
tggagaaaaa ctgtggagga aaccatcaag aacgaattcc ctacattgaa ggttcaacat    1440
caattgattg attctgccgc catgatccta gttaagaacc caacccacct aaatggtatt    1500
ataatcacca gcaacatgtt tggtgatatc atctccgatg aagcctccgt tatcccaggt    1560
tccttgggtt tgttgccatc tgcgtccttg gcctcttttg cagacaagaa caccgcattt    1620
ggtttgtacg aaccatgcca cggttctgct ccagatttgc caaagaataa ggtcaaccct    1680
atcgccacta tcttgtctgc tgcaatgatg ttgaaattgt cattgaactt gcctgaagaa    1740
ggtaaggcca ttgaagatgc agttaaaaag gttttggatg caggcatcag aactggtgat    1800
ttaggtggtt ccaacagtac caccgaagtc ggtgatgctg tcgccgaaga agttaagaaa    1860
atccttgctt aaaaagattc tcttttttta tgatatttgt acataaactt tataaatgaa    1920
attcataata gaaacgacac gaaattacaa aatggaatat gttcataggg taacgctatg    1980

```
atccaatatc aaaggaaatg atagcattga aggatgagac taatccaatt gaggagtggc    2040
agcatataga acagctaaag ggtagtgctg aaggaagcat acgatacccc gcatggaatg    2100
ggataatatc acaggaggta ctagactacc tttcatccta cataaataga cgcatataag    2160
tacgcattta agcataaaca cgcactatgc cgttcttctc atgtatatat atatacaggc    2220
aacacgcaga tataggtgcg acgtgaacag tgagctgtat gtgcgcagct cgcgttgcat    2280
tttcggaagc gctcgttttc ggaaacgctt tgaagttcct attccgaagt tcctattctc    2340
tagaaagtat aggaacttca gagcgctttt gaaaaccaaa agcgctctga agtcgcactt    2400
tcaaaaaacc aaaaacgcac cggactgtaa cgagctacta aaatattgcg aataccgctt    2460
ccacaaacat tgctcaaaag tatctctttg ctatatatct ctgtgctata tccctatata    2520
acctacccat ccacctttcg ctccttgaac ttgcatctaa actcgacctc tacattttt    2580 atgtttatct ctagtattac tctttagaca aaaaaattgt agtaagaact attcatagag    2640
tgaatcgaaa acaatacgaa aatgtaaaca tttcctatac gtagtatata gagacaaaat    2700
agaagaaacc gttcataatt ttctgaccaa tgaagaatca tcaacgctat cactttctgt    2760
tcacaaagta tgcgcaatcc acatcggtat agaatataat cggggatgcc tttatcttga    2820
aaaaatgcac ccgcagcttc gctagtaatc agtaaacgcg ggaagtggag tcaggctttt    2880
tttatggaag agaaaataga caccaaagta gccttcttct aaccttaacg gacctacagt    2940
gcaaaaagtt atcaagagac tgcattatag agcgcacaaa ggagaaaaaa agtaatctaa    3000
gatgctttgt tagaaaaata gcgctctcgg gatgcatttt tgtagaacaa aaaagaagta    3060
tagattcttt gttggtaaaa tagcgctctc gcgttgcatt tctgttctgt aaaaatgcag    3120
ctcagattct ttgtttgaaa aattagcgct ctcgcgttgc attttttgttt tacaaaaatg    3180 aagcacagat tcttcgttgg taaaatagcg ctttcgcgtt gcatttctgt tctgtaaaaa    3240
tgcagctcag attctttgtt tgaaaaatta gcgctctcgc gttgcatttt tgttctacaa    3300
aatgaagcac agatgcttcg ttcaggtggc acttttcggg gaaatgtgcg cggaacccct    3360
atttgtttat ttttctaaat acattcaaat atgtatccgc tcatgagaca ataaccctga    3420
tattggtcag aattggttaa ttggttgtaa cactgacccc tatttgttta ttttttctaaa    3480 tacattcaaa tatgtatccg ctcatgagac aataaccctg ataaatgctt caataatatt    3540
gaaaaaggaa gaatatgagc catattcaac gggaaacgtc gaggccgcga ttaaattcca    3600
acatggatgc tgatttatat gggtatataat gggctcgcga taatgtcggg caatcaggtg    3660
cgacaatcta tcgcttgtat gggaagcccg atgcgccaga gttgtttctg aaacatggca    3720
aaggtagcgt tgccaatgat gttacagatg agatggtcag actaaactgg ctgacggaat    3780
ttatgccact tccgaccatc aagcatttta tccgtactcc tgatgatgca tggttactca    3840
ccactgcgat ccccggaaaa acagcgttcc aggtattaga agaatatcct gattcaggtg    3900
aaaatattgt tgatgcgctg gcagtgttcc tgcgccggtt gcactcgatt cctgtttgta    3960
attgtccttt taacagcgat cgcgtatttc gcctcgctca ggcgcaatca cgaatgaata    4020
acggtttggt tgatgcgagt gattttgatg acgagcgtaa tggctggcct gttgaacaag    4080
tctggaaaga aatgcataaa cttttgccat tctcaccgga ttcagtcgtc actcatggtg    4140
atttctcact tgataacctt attttgacg aggggaaatt aataggttgt attgatgttg    4200
gacgagtcgg aatcgcagac cgataccagg atcttgccat cctatggaac tgcctcggtg    4260
agttttctcc ttcattacag aaacggcttt ttcaaaaata tggtattgat aatcctgata    4320
tgaataaatt gcaatttcat ttgatgctcg atgagttttt ctaactcatg accaaaatcc    4380
```

-continued

```
cttaacgtga gttacgcgcg cgtcgttcca ctgagcgtca gaccccgtag aaaagatcaa    4440
aggatcttct tgagatcctt tttttctgcg cgtaatctgc tgcttgcaaa caaaaaaacc    4500
accgctacca gcggtggttt gtttgccgga tcaagagcta ccaactcttt ttccgaaggt    4560
aactggcttc agcagagcgc agataccaaa tactgttctt ctagtgtagc cgtagttagc    4620
ccaccacttc aagaactctg tagcaccgcc tacatacctc gctctgctaa tcctgttacc    4680
agtggctgct gccagtggcg ataagtcgtg tcttaccggg ttggactcaa gacgatagtt    4740
accggataag gcgcagcggt cgggctgaac ggggggttcg tgcacacagc ccagcttgga    4800
gcgaacgacc tacaccgaac tgagatacct acagcgtgag ctatgagaaa gcgccacgct    4860
tcccgaaggg agaaaggcgg acaggtatcc ggtaagcggc agggtcggaa caggagagcg    4920
cacgagggag cttccagggg gaaacgcctg gtatctttat agtcctgtcg ggtttcgcca    4980
cctctgactt gagcgtcgat ttttgtgatg ctcgtcaggg gggcggagcc tatggaaaaa    5040
cgccagcaac gcggccttt tacggttcct ggccttttgc tggccttttg ctcacatgtt    5100
ctttcctgcg ttatcccctg attctgtgga taaccgtatt accgcctttg agtgagctga    5160
taccgctcgg ggtcgtgcag gtagtttatc attatcaata ctcgccattt caaagaatac    5220
gtaaataatt aatagtagtg attttcctaa ctttatttag tcaaaaaatt agccttttaa    5280
ttctgctgta acccgtacat gcccaaaata ggggcgggt tacacagaat atataacatc    5340
gtaggtgtct gggtgaacag tttattcctg gcatccacta aatataatgg agcccgcttt    5400
ttaagctggc atccagaaaa aaaaagaatc ccagcaccaa aatattgttt tcttcaccaa    5460
ccatcagttc ataggtccat tctcttagcg caactacaga gaacaggggc acaaacaggc    5520
aaaaaacggg cacaacctca atggagtgat gcaaccagcc tggagtaaat gatgacacaa    5580
ggcaattgac ccacgcatgt atctatctca ttttcttaca ccttctatta ccttctgctc    5640
tctctgattt ggaaaaagct gaaaaaaaag gttgaaacca gttccctgaa attattcccc    5700
tacttgacta ataagtatat aaagacggta ggtattgatt gtaattctgt aaatctattt    5760
cttaaacttc ttaaattcta cttttatagt tagtcttttt tttagtttta aaacaccaga    5820
acttagtttc gacggataaa atggaaaccg gtttgtcctc ggtttgcact ttctccttcc    5880
aaacaaacta tcatacactc ctgaacccgc acaataacaa tcccaaaact tccctgctgt    5940
gttataggca cccaaagaca ccaatcaaat actcctacaa taactttcca tctaagcatt    6000
gtagcacaaa aagtttccat ttgcaaaata agtgttccga atctctgtcc atcgccaaaa    6060
attccattag ggctgccact actaatcaaa ctgaaccacc agagtctgat aatcattctg    6120
tcgccacaaa gattctgaat tttgggaagg cttgttggaa gttacaaaga ccatatacaa    6180 ttattgccgtt tacctcttgt gcctgtggtt tatttggtaa ggaactgttg cataatacaa    6240
atttaatatc ttggtcattg atggaaacgt tcaaagcatt ttttttctta gtcgctatcc    6300
tttgtattgc ttctttcacc accactatca accagattta cgacttacat attgacagaa    6360
ttaacaagcc agatttgcca ctggcttcgg gcgagatttc cgtcaatact gcctggatca    6420
tggaaacttc tattattgtt gccttgtttg gattgataat caccataaaa atggaaacta    6480
agggtggtcc attgtatatt ttcggttact gttttggtat cttcggggc atcgtctact    6540 ctgttcctcc attcagatgg aaacaaaatc cttccacagc attcctttg aacttcctgg    6600 cgcacattat aaccaacttt acttttatt atgcctccag agccgccctg ggctgccct    6660 ttgaattacg cccctccttt acattttttac tggccttcat ggagaccaag tccatggaga    6720
```

```
ctggttctgc tctcgcgttg atcaaagatg cttccgatgt ggaaggtgac accaaatttg    6780
gtatatccac tttggccagc aagtatggtt ccaggaattt gaccctattt tgttctggta    6840
tcgtgctgct gtcttatgtt gcagccatct tggctggcat catttggcca caggctttca    6900
attcaaatgt tatggagacg ctgctctcgc atgctatttt ggcattttgg ttgattctac    6960
agacaagaga ttttgcttta accaattatg acccagaagc tggtagaaga ttttacgaat    7020
ttatggaaac atggaaatta tactatgctg aatatttagt gtacgttttc attggggcg    7080
gctccagcgc cggcggcggc tcttctgcgg gcggttggtc tcatccacaa tttgagaaag    7140
gtgggtcgtc tggcggcggc agcggggggcg ggtccggcgg ggggagcggc ggtatgaaat    7200
gttcgacctt ctcttttttgg tttgtctgta aaataatttt ttttttcttc agctttaaca    7260
ttcaaaccag cattgcaaat ccaagagaaa atttcttgaa atgcttttca caatatatcc    7320
ccaataatgc tactaacttg aagctagttt atactcaaaa caacccttg tacatgtccg    7380
tgctcaactc caccattcac aacctaagat tcacttcaga cactacccca aaaccattag    7440
ttattgtgac accttctcac gtttcacata tccaaggtac tattttatgc tccaagaagg    7500
tcggcctgca aattagaact agatctggag gtcatgattc agaaggaatg tcttacatct    7560
ctcaagttcc atttgtgatt gtcgatttaa gaaatatgag gagcattaag atcgatgttc    7620
actcccaaac ggcatgggtt gaagccggtg ccaccttggg cgaagtttac tactgggtca    7680
acgagaagaa tgaaaactta tcactagccg caggttattg tccaactgtt tgtgctggtg    7740
gccatttcgg aggcggcggc tacggtcctc taatgagaaa ctacggctta gctgctgaca    7800
atatcatcga cgctcacttg gttaacgttc atggtaaagt tttagataga aaatctatgg    7860
gtgaggatct tttctgggct ttgagaggtg gcggcgcaga atcatttggc attatcgttg    7920
cttgaagat cagattggtg gctgtcccca agtctacaat gttttctgtg aagaaaatta    7980
tggaaatcca tgaattggtc aaactggtga ataaatggca aaacatagct tacaagtacg    8040
ataaagactt gctgttaatg acacattta ttaccaggaa catcactgat aaccaaggca    8100
agaacaagac tgcaattcat acttattttt cctccgtttt tttgggtggt gtcgactccc    8160
tcgtggatct gatgaataaa tcattccctg aactaggtat taaaaaaacc gattgtagac    8220
aattgagttg gattgatacc atcatattct acagtggtgt tgttaattat gatactgaca    8280
acttcaacaa agaaatactg ctggaccgtt ccgccggcca gaatggtgct tttaaaatca    8340
agttggatta tgtgaaaaag cctattccag aatccgtatt tgttcaaata ttggaaaagc    8400
tgtatgaaga agacattggt gcaggcatgt acgctctta tccttatggc ggcataatgg    8460
atgaaatttc tgaaagtgcc attcctttcc cacatagggc cgggatcctg tacgagttat    8520
ggtacatttg ttcatgggaa aagcaagaag ataatgaaaa acatttaaat tggataagaa    8580
atatttataa ttttatgact ccatacgtct ccaaaaaccc acgcctggca tatttgaatt    8640
acagagacct ggatattggc atcaatgatc ctaaaaaccc aaataattac actcaggcaa    8700
gaatatgggg tgaaaaatat ttcggcaaaa attttgatag ctggtcaag gttaaaacac    8760
tggttgatcc aaacaatttc tttagaaacg aacaatctat cccacctctg cctagacata    8820
gacacggcgg tggaagcagt ggaggcggct ctattgaatc tgatgtttaa tga           8873
```

<210> SEQ ID NO 35
<211> LENGTH: 6677
<212> TYPE: DNA
<213> ORGANISM: Artificial Sequence
<220> FEATURE:
<223> OTHER INFORMATION: Synthetic

<400> SEQUENCE: 35

```
ggttaaatca tgtaattagt tatgtcacgc ttacattcac gccctccccc cacatccgct      60
ctaaccgaaa aggaaggagt tagacaacct gaagtctagg tccctattta ttttttata     120
gttatgttag tattaagaac gttatttata tttcaaattt ttcttttttt tctgtacaga    180
cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300
ttttttttta ttctttttttt tgatttcggt ttctttgaaa ttttttttgat tcggtaatct   360
ccgaacagaa ggaagaacga aggaaggagc acagacttag attggtatat atacgcatat    420
gtagtgttga agaaacatga aattgcccag tattcttaac ccaactgcac agaacaaaaa    480
ccagcaggaa acgaagataa atcatgtcga aagctacata taaggaacgt gctgctactc    540
atcctagtcc tgttgctgcc aagctatta atatcatgca cgaaaagcaa acaaacttgt     600
gtgcttcatt ggatgttcgt accaccaagg aattactgga gttagttgaa gcattaggtc    660
ccaaaatttg tttactaaaa acacatgtgg atatcttgac tgattttttcc atggagggca   720
cagtaagcc gctaaaggca ttatccgcca agtacaattt tttactcttc gaagatagaa     780
aatttgctga cattggtaat acagtcaaat tgcagtactc tgcgggtgta tacagaatag    840
cagaatgggc agacattacg aatgcacacg gtgtggtggg cccaggtatt gttagcggtt    900
tgaagcaggc ggcagaagaa gtaacaaagg aacctagagg ccttttgatg ttagcagaat    960
tgtcatgcaa gggctcccta tctactggag aatatactaa gggtactgtt gacattgcga   1020
aaagcgacaa agattttgtt atcggcttta ttgctcaaag agacatgggt ggaagagatg   1080
aaggttacga ttggttgatt atgacacccg gtgtgggttt agatgacaag ggagatgcat   1140
tgggtcaaca gtatagaacc gtggatgatg ttgtctctac aggatctgac attattattg   1200
ttggaagagg actatttgca aagggaaggg atgctaaggt agagggtgaa cgttacagaa   1260
aagcaggctg ggaagcatat ttgagaagat gcggccagca aaactaaaaa actgtattat   1320
aagtaaatgc atgtatacta aactcacaaa ttagagcttc aatttaatta tatcagttat   1380
tacccacgct atgatccaat atcaaaggaa atgatagcat tgaaggatga gactaatcca   1440
attgaggagt ggcagcatat agaacagcta aagggtagtg ctgaaggaag catacgatac   1500
cccgcatgga atgggataat atcacaggag gtactagact acctttcatc ctacataaat   1560
agacgcatat aagtacgcat ttaagcataa acacgcacta tgccgttctt ctcatgtata   1620
tatatataca ggcaacacgc agatataggt gcgacgtgaa cagtgagctg tatgtgcgca   1680
gctcgcgttg cattttcgga agcgctcgtt ttcgaaacg ctttgaagtt cctattccga    1740
agttcctatt ctctagaaag tataggaact tcagagcgct tttgaaaacc aaaagcgctc   1800
tgaagtcgca ctttcaaaaa accaaaaacg caccggactg taacgagcta ctaaaatatt   1860
gcgaataccg cttccacaaa cattgctcaa aagtatctct ttgctatata tctctgtgct   1920
atatccctat ataacctacc catccacctt tcgctccttg aacttgcatc taaactcgac   1980
ctctacattt tttatgttta tctctagtat tactctttag acaaaaaaat tgtagtaaga   2040
actattcata gagtgaatcg aaaacaatac gaaaatgtaa acatttccta tacgtagtat   2100
atagagacaa aatagaagaa accgttcata attttctgac caatgaagaa tcatcaacgc   2160
tatcactttc tgttcacaaa gtatgcgcaa tccacatcgg tatagaatat aatcggggat   2220
gcctttatct tgaaaaaatg cacccgcagc ttcgctagta atcagtaaac gcgggaagtg   2280
```

```
gagtcaggct ttttttatgg aagagaaaat agacaccaaa gtagccttct tctaaccttta      2340 acggacctac agtgcaaaaa gttatcaaga gactgcatta tagagcgcac aaaggagaaa       2400
aaaagtaatc taagatgctt tgttagaaaa atagcgctct cgggatgcat ttttgtagaa       2460
caaaaaagaa gtatagattc tttgttggta aaatagcgct ctcgcgttgc atttctgttc       2520
tgtaaaaatg cagctcagat tctttgtttg aaaaattagc gctctcgcgt tgcatttttg       2580
ttttacaaaa atgaagcaca gattcttcgt tggtaaaata gcgctttcgc gttgcatttc       2640
tgttctgtaa aaatgcagct cagattcttt gtttgaaaaa ttagcgctct cgcgttgcat       2700
ttttgttcta caaatgaag cacagatgct tcgttcaggt ggcacttttc ggggaaatgt        2760
gcgcggaacc cctatttgtt tattttttcta atacattca aatatgtatc cgctcatgag       2820 acaataacccc tgatattggt cagaattggt taattggttg taacactgac ccctatttgt     2880 ttattttttct aaatacattc aaatatgtat ccgctcatga caataaccc ctgataaatg       2940 cttcaataat attgaaaaag gaagaatatg agtattcaac atttccgtgt cgcccttatt       3000
cccttttttg cggcattttg ccttcctgtt tttgctcacc cagaaacgct ggtgaaagta       3060
aaagatgctg aagatcagtt gggtgcacga gtgggttaca tcgaactgga tctcaacagc      3120
ggtaagatcc ttgagagttt tcgccccgaa gaacgttttc caatgatgag cacttttaaa      3180
gttctgctat gtggcgcggt attatcccgt attgacgccg ggcaagagca actcggtcgc      3240
cgcatacact attctcagaa tgacttggtt gagtactcac cagtcacaga aaagcatctt      3300
acggatggca tgacagtaag agaattatgc agtgctgcca taaccatgag tgataacact      3360
gcggccaact tacttctgac aacgatcgga ggaccgaagg agctaaccgc ttttttgcac      3420
aacatggggg atcatgtaac tcgccttgat cgttgggaac cggagctgaa tgaagccata      3480
ccaaacgacg agcgtgacac cacgatgcct gtagcgatgg caacaacgtt gcgcaaacta      3540
ttaactggcg aactacttac tctagcttcc cggcaacaat taatagactg gatggaggcg      3600
gataaagttg caggaccact tctgcgctcg gcccttccgg ctggctggtt tattgctgat      3660
aaatccggag ccggtgagcg tggttctcgc ggtatcatcg cagcgctggg gccagatggt      3720
aagccctccc gtatcgtagt tatctacacg acggggagtc aggcaactat ggatgaacga      3780
aatagacaga tcgctgagat aggtgcctca ctgattaagc attggtaact catgaccaaa      3840
atcccttaac gtgagttacg cgcgcgtcgt tccactgagc gtcagacccc gtagaaaaga      3900
tcaaaggatc ttcttgagat ccttttttc tgcgcgtaat ctgctgcttg caaacaaaaa       3960
aaccaccgct accagcggtg gtttgtttgc cggatcaaga gctaccaact cttttttccga     4020 aggtaactgg cttcagcaga gcgcagatac caaatactgt tcttctagtg tagccgtagt      4080
tagcccacca cttcaagaac tctgtagcac cgcctacata cctcgctctg ctaatcctgt      4140
taccagtggc tgctgccagt ggcgataagt cgtgtcttac cgggttggac tcaagacgat      4200
agttaccgga taaggcgcag cggtcgggct gaacggggggg ttcgtgcaca cagcccagct    4260
tggagcgaac gacctacacc gaactgagat acctacagcg tgagctatga gaaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc agggggggcgg agcctatgga   4500 aaaacgccag caacgcggcc tttttacggt tcctggcctt ttgctggcct ttgctcaca    4560 tgttctttcc tgcgttatcc cctgattctg tggataaccg tattaccgcc tttgagtgag    4620
ctgataccgc tcgggtcgt gcaggtatag cttcaaaatg tttctactcc tttttttactc    4680
```

```
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800 gaaagaaaa aagtgaccgc ctcgtttctt tttcttcgtc gaaaaggca ataaaaattt      4860 ttatcacgtt tctttttctt gaaatttttt tttttgatt tttttctctt tcgatgacct    4920
cccattgata tttaagttaa taaacggact tcaatttctc aagtttcagt ttcattttc    4980 ttgttctatt acaactttt ttacttcttg ctcattagaa agaaagcata gcaatctaat    5040
ctaagtttaa aatgaatcat ttgagagcag aagggcctgc ttccgtgctg ctattggta    5100 ccgccaatcc agaaaatatc ctgctgcagg acgaattccc agattactat tttagggtca   5160
ccaaatctga acatatgaca caattgaaag agaaattcag aaagatttgt gacaagtcca   5220
tgattaggaa aagaaattgt tttttgaatg aagaacactt gaagcaaaat cctcgcctgg   5280
tggagcatga atgcaaact ttggatgcta gacaagacat gttggtggtg aagttccaa     5340 agctggggaa ggatgcctgt gccaaggcca ttaaagaatg gggccaacca aaatccaaaa   5400
ttacccacct gattttcacc tccgcctcca ccactgatat gccaggtgca gactatcatt   5460
gtgctaaatt gttgggtttg tcccctccg tgaagagagt tatgatgtat caattaggtt    5520
gttatggcgg cggcaccgtt ctgagaattg ccaaagacat tgctgaaaac aataaggtg    5580 cgcgcgtttt ggctgtttgt tgtgatatta tggcatgttt atttagaggt ccaagtgaaa   5640
gtgacttgga attgctagtg ggccaggcca tatttggtga tggtgccgct gctgtgatcg   5700
ttggtgctga gcctgatgaa tctgtcggtg aaagaccaat ttttgaactg gtttccactg   5760
gtcaaaccat tttgccaaat tcagaaggta ctattggcgg ccatatcaga gaagctggtt   5820
taatctttga tttgcacaag gatgtcccaa tgttaatttc caataatatt gaaaaatgtt   5880
tgatcgaagc atttaccccc atcggtattt ctgattggaa ttccatcttc tggattacac   5940
atcctggcgg taaagctatc ttagataaag ttgaggagaa gttgcattta aagtctgaca   6000
aatttgttga ttcaagacat gtcctgtctg agcacggtaa tatgtcttcc tcgaccgtct   6060
tgtttgtcat ggatgagttg aggaagaggt ccctggaaga aggcaagagc accaccggtg   6120
acggttttga gtgggggggtc ctctttggat ttgggccagg cctgaccgta gaaagggttg   6180
ttgtccgctc ggtgccaatc aaatatggtg gggggtccag cgccggtggc gggagctccg   6240
cgggcggttg gtctcaccca caatttgaaa agggtggcag cagcggcggc ggctctggcg   6300
gaggctccgg cggggggctcg gggggtatgg ctgtcaagca tctgatcgtg ctgaagttca   6360
aagatgaaat tactgaagcc caaaaggagg aattttcaa gacatatgtt aatttggtta    6420
acatcattcc agcaatgaaa gatgtttatt ggggtaagga cgttactcaa aaaaataagg   6480
aagagggtta cactcatatt gttgaagtca ctttcgaatc cgtcgaaaca attcaagatt   6540
atattattca tccagctcat gttgggtttg gcgatgtgta cagatcattt tgggaaaaat   6600
tattgatttt tgactacaca ccaagaaaag gcggtggaag cagtggaggc ggctctattg   6660
aatctgatgt ttaatag                                                  6677
```

<210> SEQ ID NO 36
<211> LENGTH: 3372
<212> TYPE: DNA
<213> ORGANISM: Artificial Sequence
<220> FEATURE:
<223> OTHER INFORMATION: Synthetic

<400> SEQUENCE: 36

```
atggagaaga ctcaagaaac agtccaaaga attcttctag aaccctataa atacttactt    60
cagttaccag gtaaacaagt gagaaccaaa cttccacagg catttaatca ttggctgaaa   120
```

| | |
|---|---|
| atggagaaga ctcaagaaac agtccaaaga attcttctag aaccctataa atacttactt | 60 |
| cagttaccag gtaaacaagt gagaaccaaa ctttcacagg catttaatca ttggctgaaa | 120 |
| gttccagagg acaagctaca gattattatt gaagtgacag aaatgttgca taatgccagt | 180 |
| ttactcatcg atgatattga agacaactca aaactccgac gtggcttttcc agtggcccac | 240 |
| agcatctatg gaatcccatc tgtcatcaat tctgccaatt acgtgtattt ccttggcttg | 300 |
| gagaaagtct taacccttga tcacccagat gcagtgaagc ttttacccg ccagcttttg | 360 |
| gaactccatc agggacaagg cctagatatt tactggaggg ataattacac ttgtcccact | 420 |
| gaagaagaat ataagctat ggtgctgcag aaaacaggtg gactgtttgg attagcagta | 480 |
| ggtctcatgc agttgttctc tgattacaaa gaagatttaa aaccgctact taatacactt | 540 |
| gggctctttt tccaaattag ggatgattat gctaatctac actccaaaga atatagtgaa | 600 |
| aacaaaagtt tttgtgaaga tctgacagag ggaaagttct catttcctac tattcatgct | 660 |
| atttggtcaa ggcctgaaag cacccaggtg cagaatatct tgcgccagag aacagaaaac | 720 |
| atagatataa aaaatactg tgtacattat cttgaggatg taggttcttt tgaatacact | 780 |
| cgtaataccc ttaaagagct tgaagctaaa gcctataaac agattgatgc acgtggtggg | 840 |
| aaccctgagc tagtagcctt agtaaaacac ttaagtaaga tgttcaaaga gaaaatgaa | 900 |
| ggcggttctg gcagcggaga gggcagagga agtcttctaa catgcggtga cgtggaggag | 960 |
| aatcccggcc ctaggtctgg cagcggagag ggcagaggag gtcttctaac atgcggtgac | 1020 |
| gtggaggaga atcccggccc taggacacaa aagaaagtcc cagacaattg ttgtagacgt | 1080 |
| gaacctatgc tggtcagaaa taaccagaaa tgtgattcag tagaggaaga cagggata | 1140 |
| aaccgagaaa gaaaagttga ggttataaaa cccttagtgg ctgaaacaga taccccaaac | 1200 |
| agagctacat ttgtggttgg taactcctcc ttactcgata cttcatcagt actggtgaca | 1260 |
| caggaacctg aaattgaact tcccagggaa cctcggccta atgaagaatg tctacagata | 1320 |
| cttgggaatg cagagaaagg tgcaaaattc cttagtgatg ctgagatcat ccagttagtc | 1380 |
| aatgctaagc atatcccagc ctacaagttg gaaactctga tggaaactca tgagcgtggt | 1440 |
| gtatctattc gccgacagtt acttccaag aagctttcag aaccttcttc tctccagtac | 1500 |
| ctaccttaca gggattataa ttactccttg gtgatgggag cttgttgtga aatgttatt | 1560 |
| ggatatatgc ccatccctgt tggagtggca ggacccttt gcttagatga aaagaattt | 1620 |
| caggttccaa tggcaacaac agaaggttgt cttgtggcca gcaccaatag aggctgcaga | 1680 |
| gcaataggtc ttggtggagg tgccagcagc cgagtccttg cagatgggat gactcgtggc | 1740 |
| ccagttgtgc gtcttccacg tgcttgtgac tctgcagaag tgaaagcctg gctcgaaaca | 1800 |
| tctgaagggt tcgcagtgat aaaggaggca tttgacagca ctagcagatt tgcacgtcta | 1860 |
| cagaaacttc atacaagtat agctggacgc aacctttata tccgtttcca gtccaggtca | 1920 |
| ggggatgcca tggggatgaa catgatttca aagggtacag agaaagcact ttcaaaactt | 1980 |
| cacgagtatt tccctgaaat gcagattcta gccgttagtg gtaactattg tactgacaag | 2040 |
| aaacctgctg ctataaattg gatagaggga agaggaaaat ctgttgtttg tgaagctgtc | 2100 |
| attccagcca aggttgtcag agaagtatta aagactacca cagaggctat gattgaggtc | 2160 |
| aacattaaca gaatttagt gggctctgcc atggctggga catagagg ctacaacgcc | 2220 |
| catgcagcaa acattgtcac cgccatctac attgcctgtg acaggatgc agcacagaat | 2280 |
| gttggtagtt caaactgtat tactttaatg gaagcaagtg gtcccacaaa tgaagattta | 2340 |
| tatatcagct gcaccatgcc atctatagag ataggaacgg tgggtggtgg gaccaaccta | 2400 |

```
ctacctcagc aagcctgttt gcagatgcta ggtgttcaag gagcatgcaa agataatcct   2460
ggggaaaatg cccggcagct tgcccgaatt gtgtgtggga ccgtaatggc tggggaattg   2520
tcacttatgg cagcattggc agcaggacat cttgtcaaaa gtcacatgat tcacaacagg   2580
tcgaagatca atttacaaga cctccaagga gcttgcacca agaagacagc cggctcagga   2640
ggttcttcag gactggaagt gctgtttcag ggcccgggtg gatctggcat gatgcctgaa   2700
ataaacacta accacctcga caagcaacag gttcaactcc tggcagagat gtgtatcctt   2760
attgatgaaa atgacaataa aattggagct gagaccaaga agaattgtca cctgaacgag   2820
aacattgaga aaggattatt gcatcgagct tttagtgtct tcttattcaa caccgaaaat   2880
aagcttctgc tacagcaaag atcagatgct aagattacct ttccaggttg ttttacgaat   2940
acgtgttgta gtcatccatt aagcaatcca gccgagcttg aggaaagtga cgcccttgga   3000
gtgaggcgag cagcacagag acggctgaaa gctgagctag gaattccctt ggaagaggtt   3060
cctccagaag aaattaatta tttaacacga attcactaca aagctcagtc tgatggtatc   3120
tggggtgaac atgaaattga ttacattttg ttggtgagga agaatgtaac tttgaatcca   3180
gatcccaatg agattaaaag ctattgttat gtgtcaaagg aagaactaaa agaacttctg   3240
aaaaaagcag ccagtggtga aattaagata acgccatggt ttaaaattat tgcagcgact   3300
tttctcttta aatggtggga taacttaaat catttgaatc agtttgttga ccatgagaaa   3360
atatacagaa tg                                                      3372
```

ISOLATED CODON SEQUENCE

CROSS-REFERENCE TO RELATED APPLICATIONS

The present application is a divisional of U.S. Ser. No. 15/719,430, filed on Sep. 28, 2017 entitled "An Isolated Codon Optimized Nucleic Acid" and issued as U.S. Pat. No. 10,435,727 on Oct. 8, 2019, which is a continuation of U.S. Ser. No. 15/096,164, filed Apr. 11, 2016, entitled "A Novel Method for the Cheap, Efficient, and Effective Production of Pharmaceutical and Therapeutic API's, Intermediate, and Final Products" and now abandoned, that claims the benefit of U.S. Provisional Patent Application Ser. No. 62/145,430, entitled "A Novel Method for the Cheap, Efficient, and Effective Production of Pharmaceutical and Therapeutic API's, Intermediate, and Final Products", filed Apr. 9, 2015, all of which are herein incorporated by reference in their entirety for all purposes.

The Sequence Listing, which is a part of U.S. Ser. No. 15/719,430, filed on Sep. 28, 2017 entitled "An Isolated Codon Optimized Nucleic Acid", includes a computer readable form and a written sequence listing comprising nucleotide and/or amino acid sequences of the present application. The sequence listing information recorded in computer readable form is identical to the written sequence listing. The ASCII text file, entitled "SeqListIsolatedCodonSequenceD2.txt" was created on Oct. 27, 2019 using PatentIn version 3.5 and is incorporated herein by reference in its entirety. The subject matter of the Sequence Listing is incorporated herein by reference in its entirety.

FIELD OF INVENTION

The present invention is in the technical field of large scale production of pharmaceutical and supplemental products for various common illnesses, medical conditions, and general industrial use. More particularly, the present invention is in the technical field of bio-synthesis of cannabinoids, terpenoids, stilbenoids, flavonoids, phenolic amides, lignanamides, spermidine alkaloids, and phenylpropanoids; compounds found in *Cannabis sativa*, along with various combinations and specialized formulations which are beneficial in ailments ranging from cancer to glaucoma. The final product(s) can be an intermediate or a compound of interest. The core concept of the invention is based on the idea of cheaper and more efficient production, along with novel products and applications.

INTRODUCTION

Cannabinoids from *cannabis* have been used for thousands of years for treatment of various ailments and conditions in many different cultures around the world. However, most of various types of cannabinoids in *cannabis* are at a very low concentration in the plant. Therefore, most patients/users never get a threshold dosage for any kind of relief from anything other than tetrahydrocannabinolic acid (THC/A), cannabinolic-acid (CBD/A), and cannabinol (CBN). There are a few strains or concentrates available that have a rare cannabinoid, but are usually very highly concentrated in tetrahydrocannabinol (THC) or cannabidiol (CBD) to have any pronounced effect by the rare cannabinoid.

In other words, the pharmaceutical industry has not tapped into the real potential of the *cannabis* plant. With time, more research is being conducted into the different kinds of cannabinoids and their medicinal applications. Researchers are finding that many of the other cannabinoids also have unique medicinal properties.

SUMMARY

Biosynthesis of important molecules can be used for therapeutic applications, bulk substance production, intermediate API biosynthesis, and various other novel formulations and applications for such substances, as known to those skilled in the art. Many biological molecules can be changed/converted into molecules of importance by using enzymes and other processes. This process can be utilized by employing methods for transforming a range of starting materials into final products to be used in pharmaceuticals and supplements as active ingredients, or donating a significant portion of their structure to the final active ingredients. The final products can also be used in other industries and applications, such as food, beverage, and other goods production. For example, table sugar, starch, and cellulose can be converted to glucose, creating a molecule that can readily be utilized by any organism as an energy source. Therefore, depending on the specific compound(s) being manufactured, and the kind(s) of starting materials available, along with the host and production technique(s) any kind of host engineering, various expression systems and methods, and varying materials, a spectrum of different methods and products is possible.

The advantages of the present invention include, without limitation, creation of hundreds of compounds from readily available biological molecules that can be produced and harvested from virtually all known sources of plants and other energy producing organisms. Since sugar producing plants and organisms, biomass, and carbon based industrial waste products are very abundant, our "raw material" will be very cheap and easy to obtain anywhere in the world. After scaling up the given methods, hundreds of compounds with medicinal properties can be produced at a very low cost, allowing the widespread distribution and aiding of millions of people.

Another advantage is that there is no need or use of growing any illegal plants. For example, no marijuana, poppy, or other plant production is necessary. This is advantageous as it will lead to drastically cutting down the production, consumption, and trafficking of many unregulated substances.

The most important advantage of the present invention is that we can make and use many compounds that are virtually so low in concentration in the *cannabis* plant, that there is no effect in using *cannabis* if we are only after the therapeutic effects of these compounds. For example, patients using marijuana can only benefit from tetrahydrocannabinolic acic (THCA), THC, cannabidiolic acid (CBDA), CBD, CBN, and a few other compound class families, as the concentrations of the other compounds is so low that it has no effect. This invention will allow the production of hundreds of compounds in pure form, leading to many new medical discoveries and applications.

BRIEF DESCRIPTION OF THE FIGURES

The nature, objects, and advantages of the present invention will become more apparent to those skilled in the art after considering the following detailed description in connection with the accompanying figures, in which like reference numerals designate like parts throughout, and wherein.

DETAILED DESCRIPTION

Figure 1:
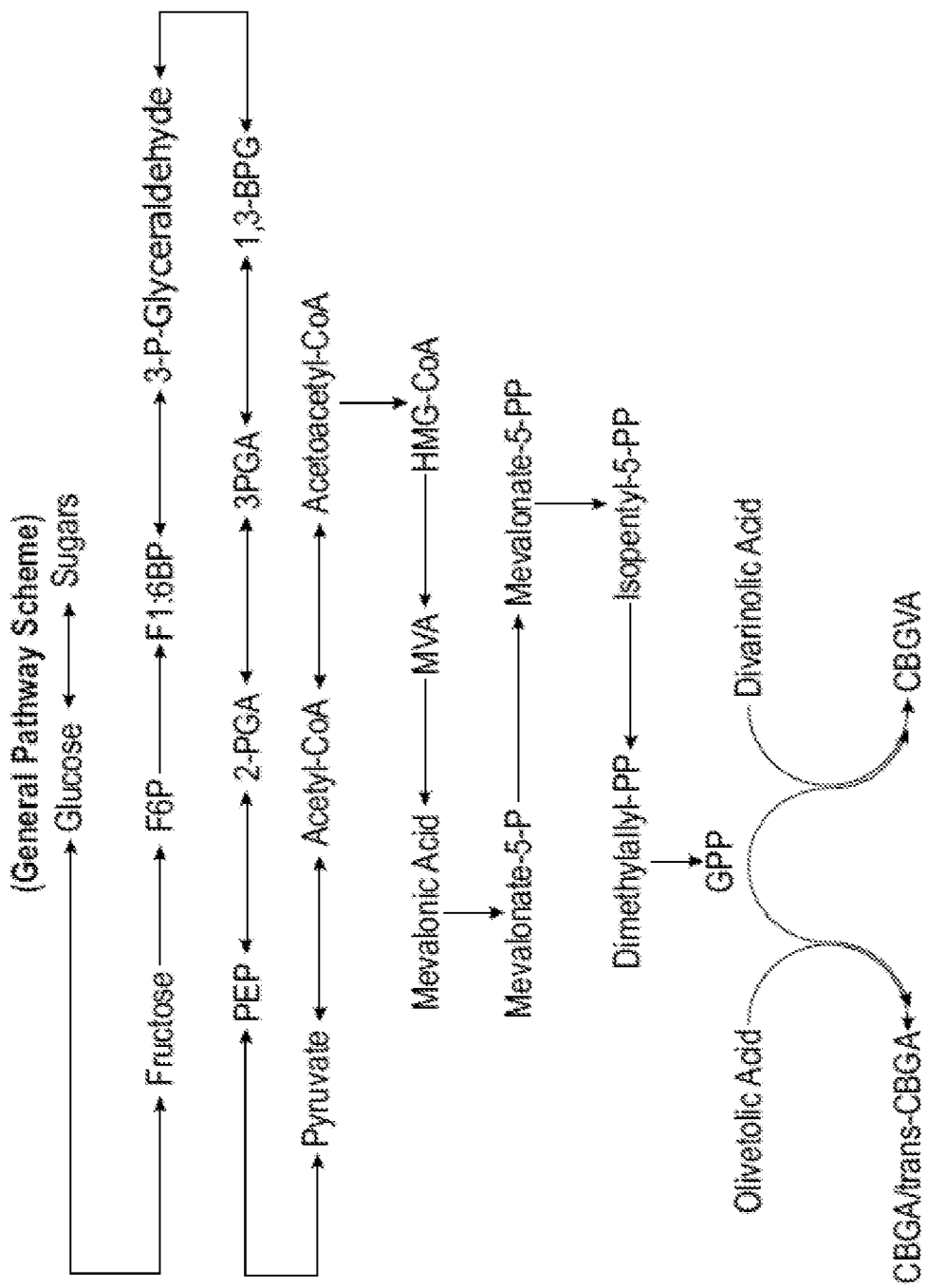
FIG. 1 is a diagram of the pathway for the biosynthesis of all molecules of interest via the conversion of starting materials to glucose and then to final products.

The present invention is a method for the biosynthesis of hundreds of compounds, mainly found in the *cannabis* plant. The starting material for these compounds can be any biological compound that is used/produced in a biological organism from the sugar family starting materials or other low cost raw materials processed via enzymes or within organisms to give final products. These final products include, but are not limited to: cannabinoids, terpenoids, stilbenoids, flavonoids, phenolic amides, lignanamides, spermidine alkaloids, and phenylpropanoids (collectively, "final products").

Definitions, Terms, Elements

The Following are a List and their Definitions:

Genetic engineering: targeted manipulation of a cell's genetic information;

Rational Metabolic Engineering: engineering of enzymes, transporters, or regulatory proteins based on available information about enzymes, pathways, and their regulation.

Evolutionary engineering: encompasses all methods for empirical strain improvement (mutagenesis [natural or induced] and recombination and/or shuffling of genes, pathways, and even whole cells; usually performed in cycles or sequentially Cannabinoids: compounds that are terpenophenolic with 22 carbons (21 carbons for neutral forms), found in *cannabis*

Terpenoids: also known as isoprenoids, class of organic compounds

Stilbenoids: hydroxylated derivatives of stilbene

Flavonoids/phenylpropanoids: compounds derived from or using phenylalanine as a precursor Lignanamides/phenolic amides: compounds produced through tyramine pathways Spermidine alkaloids: compounds produced through glutamic acid pathways Starting material/reactant/excipient: compounds used for the initial step of biosynthesis, which are cheap and readily available Intermediate: products that are formed within the biosynthesis pathways, which can further be processed to make final products, or can, themselves, be utilized as a final product Final product/product/end product/compounds of interest: cannabinoids, terpenoids, stilbenoids, flavonoids, phenolic amides, lignanamides, spermidine alkaloids, and phenylpropanoids In-vivo: inside the cell In-vitro: outside the cell BAC: bacterial artificial chromosome, carrier of DNA of interest into host YAC: yeast artificial chromosome, carrier of DNA of interest into host Vector/cosmid/phage: carrier of DNA of interest into host Starting Materials All biological organisms produce organic molecules that are processed in many different processes in the organism. The present invention utilizes starting materials that are either:

1) Readily available and relatively pure
2) Cheap to produce or buy
3) Easily modified (via enzymes, catalysts, or other methods)

Based on the above criteria, there are multiple groups and families of compounds that would fit one or all three of the above criteria. These groups and families of compounds include, but are not limited to: ligno-cellulosic biomass, forest biomass, energy/food production waste, but are not limited to: ligno-cellulosic biomass, forest biomass, energy/food production waste, commonly available sugar-based substrates, food and feed grains.

Sugars and metabolic intermediates from cellular processes can be used as starting materials. Sugars can be found in abundance in many substances, including, but not limited to the following: rice, soya/rape, cereals (maize), wheat, beans, sugar beet (sugar cane), plant biomass (wood), grasses, and various other sources. Starch, cellulose, fructose, ethanol, and saccharose in the aforementioned substances can be enzymatically converted to glucose, which, after filtration and purification steps, can be used as a raw material for the final products.

Subsequent steps can also be performed on the lignocellulose, which further makes hemicellulose and cellulose, both which make glucose. An advantage of this method is that there are by-products generated which can be sold as raw material to make hydrocarbons, biogas, and other fuel sources. Whole crops or parts of crops, or waste matter from crop products can be used and incorporated into this system, yielding an "eco-friendly" facility. Products made from these raw materials can use any of the starting materials listed in Table 2.

Within the realm of readily available non-biomass/crop bulk material, HFCS (high fructose corn syrup) is a cost effective syrup made with fruit sources that contains anywhere from 30-90% fructose, along with some other sugars. Plants that make molasses, HFCS, and other sugars can be genetically modified to enhance the production of sugar, leading to better yields of starting material from the crop. Other products from these plants can also be incorporated into compounds of interest production via slight system modification. Biodiesel, ethanol, glycerol, lactic acid, whey and glucose are a few others. These work due to the fact that any of these products can be converted into starting material for our own purposes using enzymatic or physiochemical tools.

Plants also have their own innate levels of metabolites that can be harvested into the process from a plant biomass source. Processes can be crafted that utilize most of the metabolites and biomass for API production giving the maximum efficiency and usability per amount of starting material used. (Enzyme combinations or chambers that utilize most intermediates, sugars, oils, etc. in each biomass load).

Biorefineries can be custom designed that cater to specific raw material (plant biomass for harvesting lignocellulose which is further processed and refined into a simple carbohydrate used in the API manufacturing processes). During certain steps throughout the process, thermochemical and other processing can be used for higher efficiencies which are not possible with biochemical processing alone.

Another group of cheap starting materials is agricultural residue, grass, aquatic biomass, and water hyacinth. Products such as oils and alcohols can be made with these bulk materials. These materials can be converted enzymatically and chemically into starting materials that can readily by injected into our API production system.

Specifically, biorefineries can be designed to be extremely efficient, using all parts of the raw material. For example, concerning plant biomass, the biomass can be step-wise processed so we are able to harvest all individual components. The first step can be using solvent to extract terpenes, alkaloids, etc. Other methods can be used to extract steroids, triglycerides, and other valuable metabolites. Finally the biomass can be treated with cellulases to give glucose, which is one of the primary raw materials of choice.

Production Roadmap Summary

The present invention is a method that covers the biosynthesis of hundreds of compounds, mainly found in the *cannabis* plant. The starting material for these compounds can be any biological compound that is used/produced in a biological organism from the sugar family starting materials or other low cost raw materials processed via enzymes or within organisms to give final products. Information related to the starting materials were detailed in the previous section.

Most sugars and related compounds can be inter-changed using various enzyme systems. For example, we can convert glucose to fructose using Fructose 6-Phosphate (F-6-P) as an intermediate.

Apart from starting materials, we can either:

1) Make enzymes via vectors in bacteria (e.g. *E. coli*) or yeast (e.g. *S. cerevisiae*), extract enzymes, and create in vitro models for making cannabinoids.

2) Make enzymes via protein synthesizing systems (Protein Synth. Robot, Cell Free Expression Systems, etc.)

3) Make final products (compounds of interest) in bacteria or yeast via vectors, plasmids, cosmids, mRNA, various RNA, etc; feed them substrate and purify product.

4) Genetically engineer strains of bacteria and yeast that specialize in cannabinoid production, or intermediate production, or substrate production, etc.

5) Use organic chemistry for certain parts of the above processes.

6) Use various plant starting material for large quantities of substrates or intermediates.

7) Genetically engineer various plants to produce cannabinoids. (e.g.

Tomatoes or celery that naturally produce cannabinoids, or algae that produces cannabinoids)

8) Using bioengineered or unengineered *C. sativa* or any other plant/algae cell lines for enzyme/substrate/intermediates/product(s) production.

9) Protein engineering on the various proteins involved in the processes; engineering will enhance the functionality, ruggedness, and efficiency of the enzymes, and altering them into a novel protein, one not found to be covered in any of the above prior art patents.

10) Genetically engineer various plant species to produce higher yielding raw material (sugars) to be used in production of the products. A possibility is to have an indoor/grow for different plants to be used as raw material producers.

After the final product is made, a purification system will filter and concentrate the target molecules. Examples include large scale filtration systems such as chromatography. Once a pure product, we can utilize liquid solutions, caps, sprays, and other delivery systems.

As many of these final products are made, their applications can be seen from glaucoma to cancer, or general well-being. Certain cofactors can be combined with certain final products for more efficacy against specific medical conditions (e.g. combine certain vitamins or other therapeutic compounds with certain compounds of interest). We can also make final products that have certain combinations of compounds of interest with other cofactors as well (e.g. combine THCA/CBDA/Vitamin C, or CBDVA/CBD). This patent covers all the products above and also ones discovered in the future based on the same principles and methods.

DETAILED DESCRIPTION OF THE FIGURES

Referring now to the invention in more detail, in FIG. 1 there is shown a family of sugars and other common derivatives. Along each arrow for each reaction, the number denotes a specific enzyme that catalyzes the reaction. Starting with any sugar in FIG. 1 (list of starting materials in Table 1), we can convert it to glucose to incorporate it into the reaction using the appropriate enzyme, as known to those skilled in the art. An unlimited number of ways are possible when dealing with any starting material, as described above. Enzymes needed for each kind of substrate can be made in vivo or in vitro just as we will be doing for the enzymes in the final product or intermediate production. The final sugar that enters our mechanism will be either glucose or fructose. Through the glycolysis pathway, the sugar will be converted into Acetyl-CoA with the addition of ATP and CoA (shown in FIG. 1). From this point on, the intermediate can follow a variety of paths that can lead to hundreds of products. There are many alternative ways of doing this. We can use the DOX, MEP or MVA pathways to get isopentenyl pyrophosphate (IPP) and DMAPP, which give us geranyl diphosphate (GPP) and NPP. For a reaction with Olivetolic Acid or Divarinolic Acid, we get many cannabinoids as final products.

Figure 2:
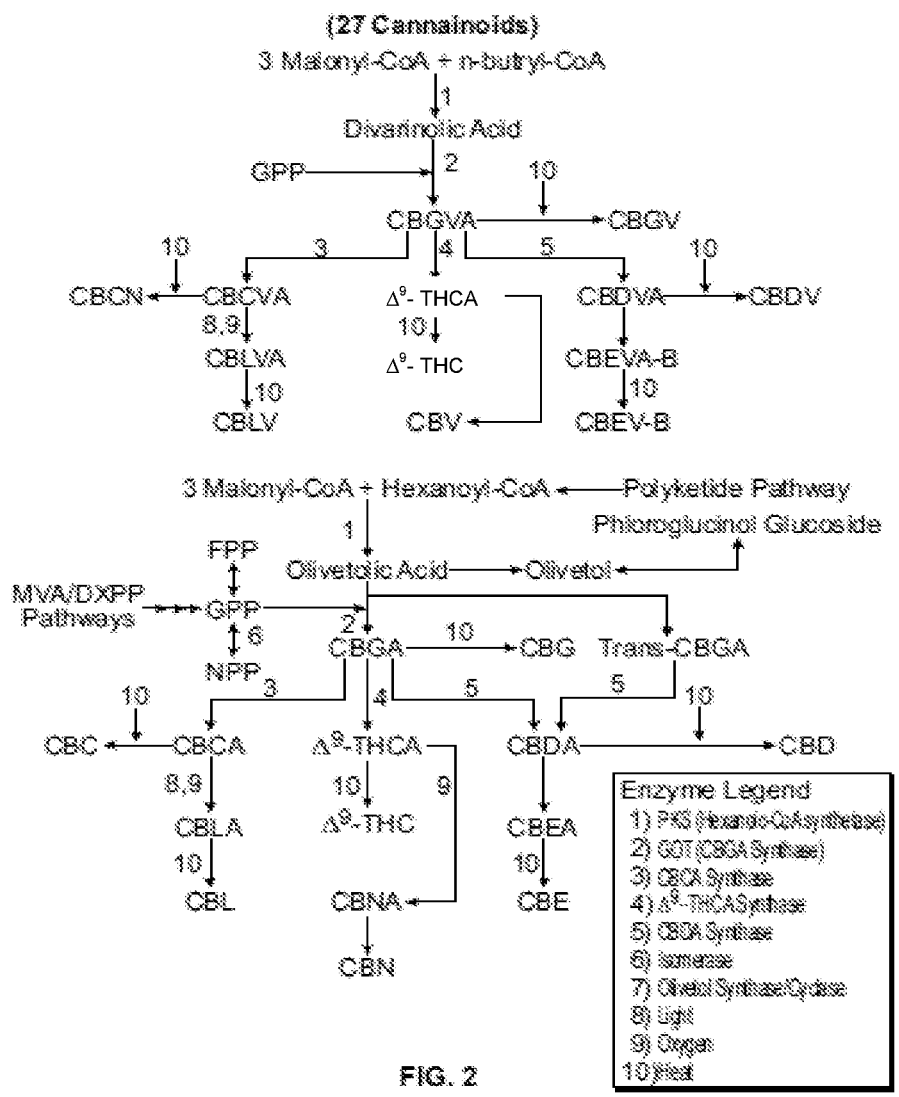
FIG. 2 is a diagram of the pathway for the biosynthesis of cannabinoids.

The generalized pathway for the production of cannabinoids once the starting material is converted to glucose is the following, using appropriate enzymes as known by those skilled in the art:

Glucose→Fructose→F-6-P→F1:6BP→3-P-Glyceraldehyde→1,3-BPG→3PGA→2-PGA→PEP→Pyruvate→Acetyl-CoA→Acetoacetyl CoA→HMG-CoA→MVA→Mevalonic Acid→Mevalonate-5-P→Mevalonate-5-PP→Isopentyl-5-PP→Dimethylallyl-PP-NPP/GPP→GPP This general pathway is outlined in FIG. 1. From this point on, the pathway can utilize Olivetolic Acid or Divarinolic Acid with GPP, yielding CBGA or CBGVA, which can further yield other cannabinoids, as shown in FIG. 2.

Figure 3:
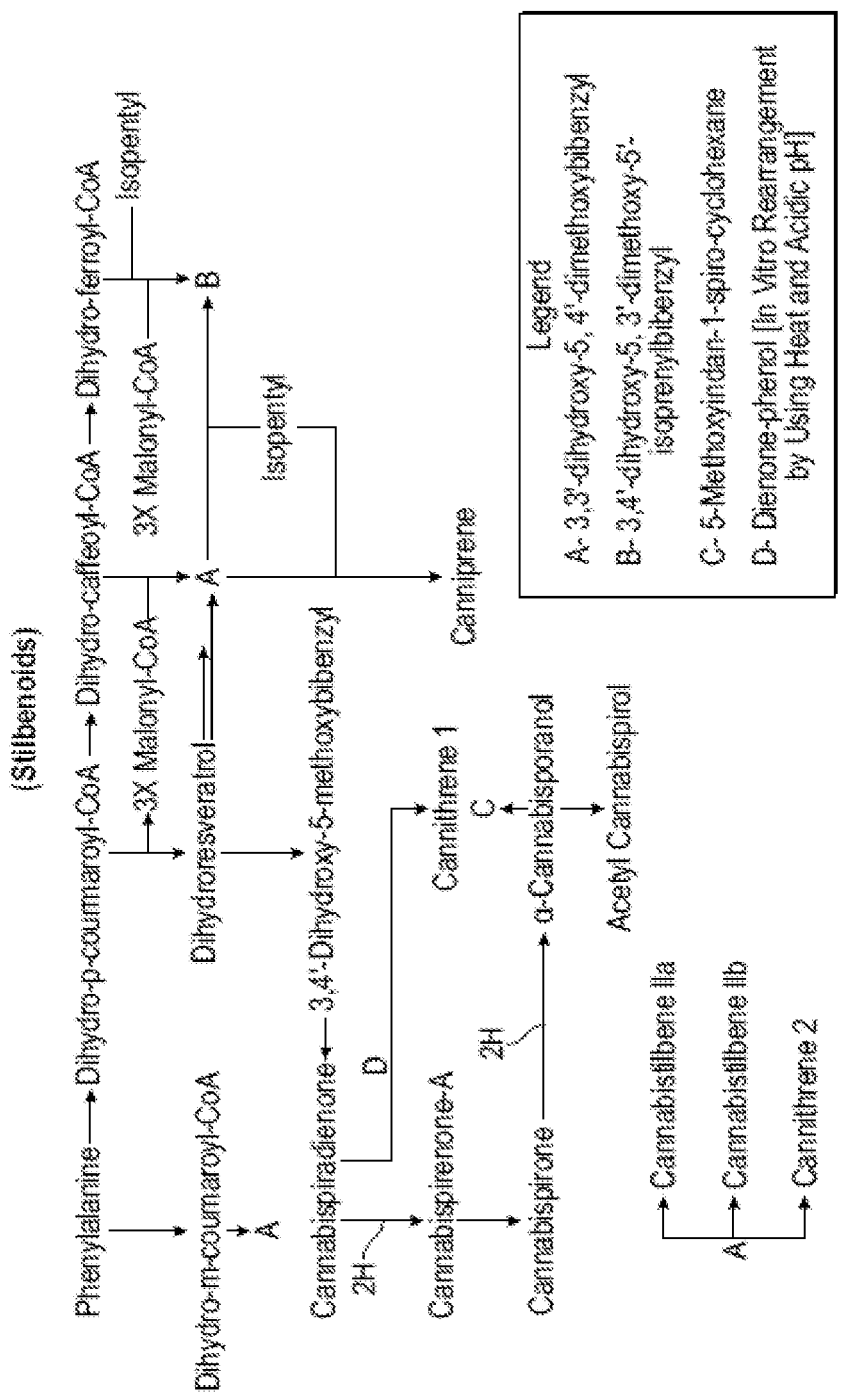
FIG. 3 is a diagram of the pathway for the biosynthesis of stilbenoids.
Figure 4:
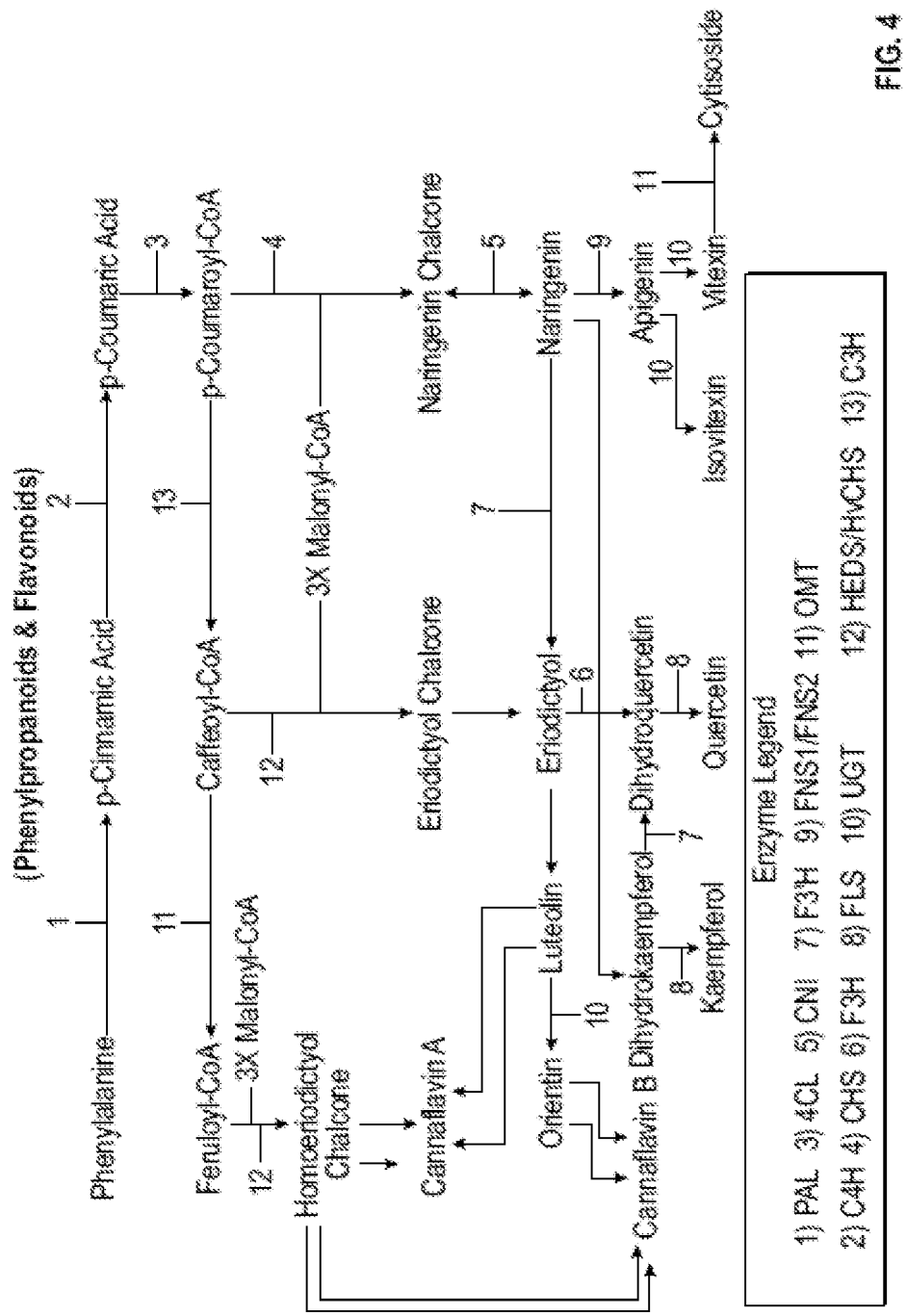
FIG. 4 is a diagram of the pathway for the biosynthesis of phenylpropanoids and flavonoids.

The pathways for stilbenoids, phenylpropanoids, and flavonoids work in a similar fashion. Phenylalanine is generated from sugars, which is then further processed into other compounds using enzymes to final compounds, as shown in FIG. 3 and FIG. 4.

Figure 5:
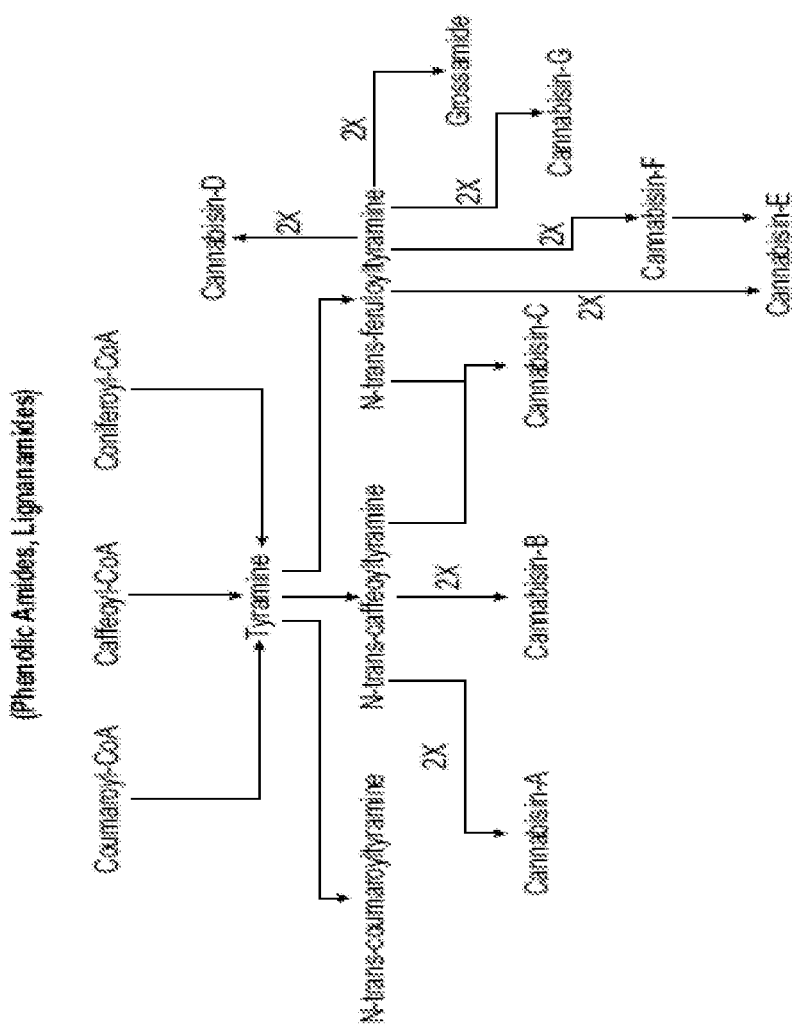
FIG. 5 is a diagram of the pathway for the biosynthesis of phenolic amides and ligananamides.
Figure 6:
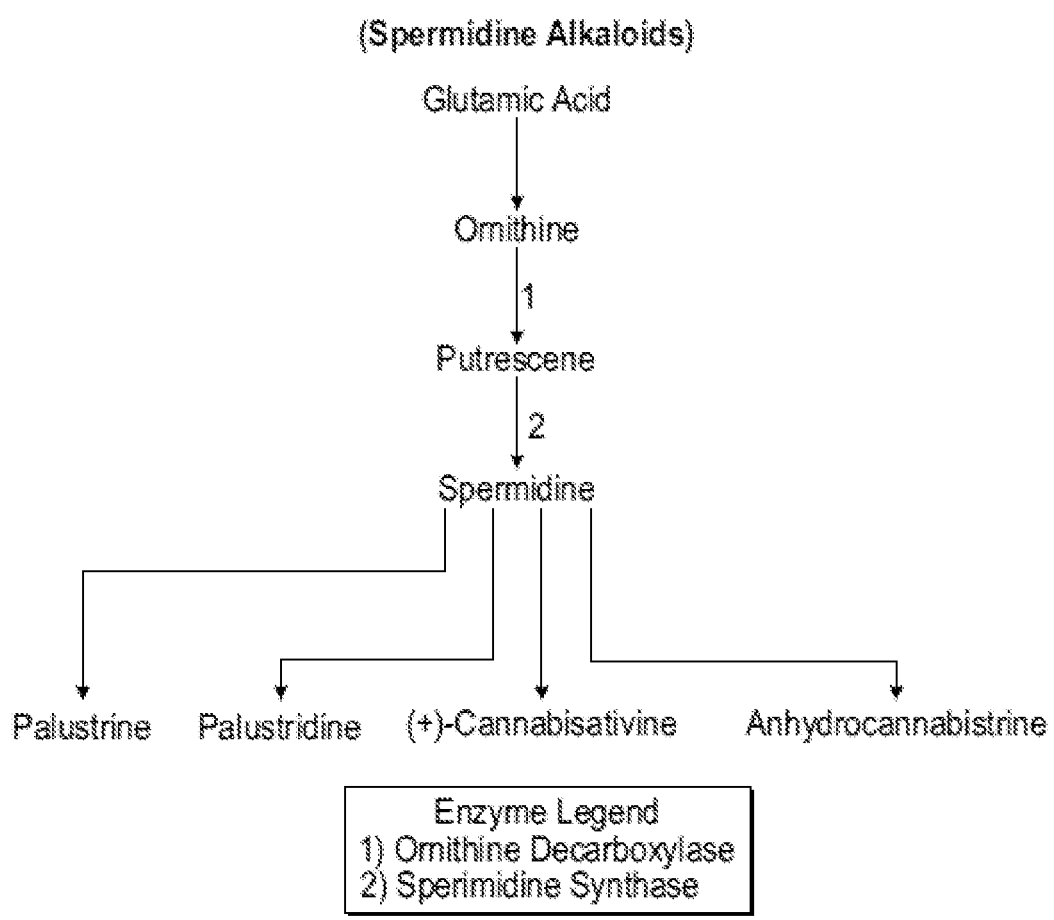
FIG. 6 is a diagram of the pathway for the biosynthesis of spermidine alkaloids.

Phenolic amides and lignanamide pathways are derived from tyramine molecules reacting with other compounds, as shown in FIG. 5. Tyramine can also be synthesized in our cells of interest as most living organisms contain the pathway to synthesize tyramine on their own. Same is the case for spermidine alkaloid production, as most cells already produce glutamic acid, which can be further processed by enzymes into the final components, as shown in FIG. 6.

Figure 7:
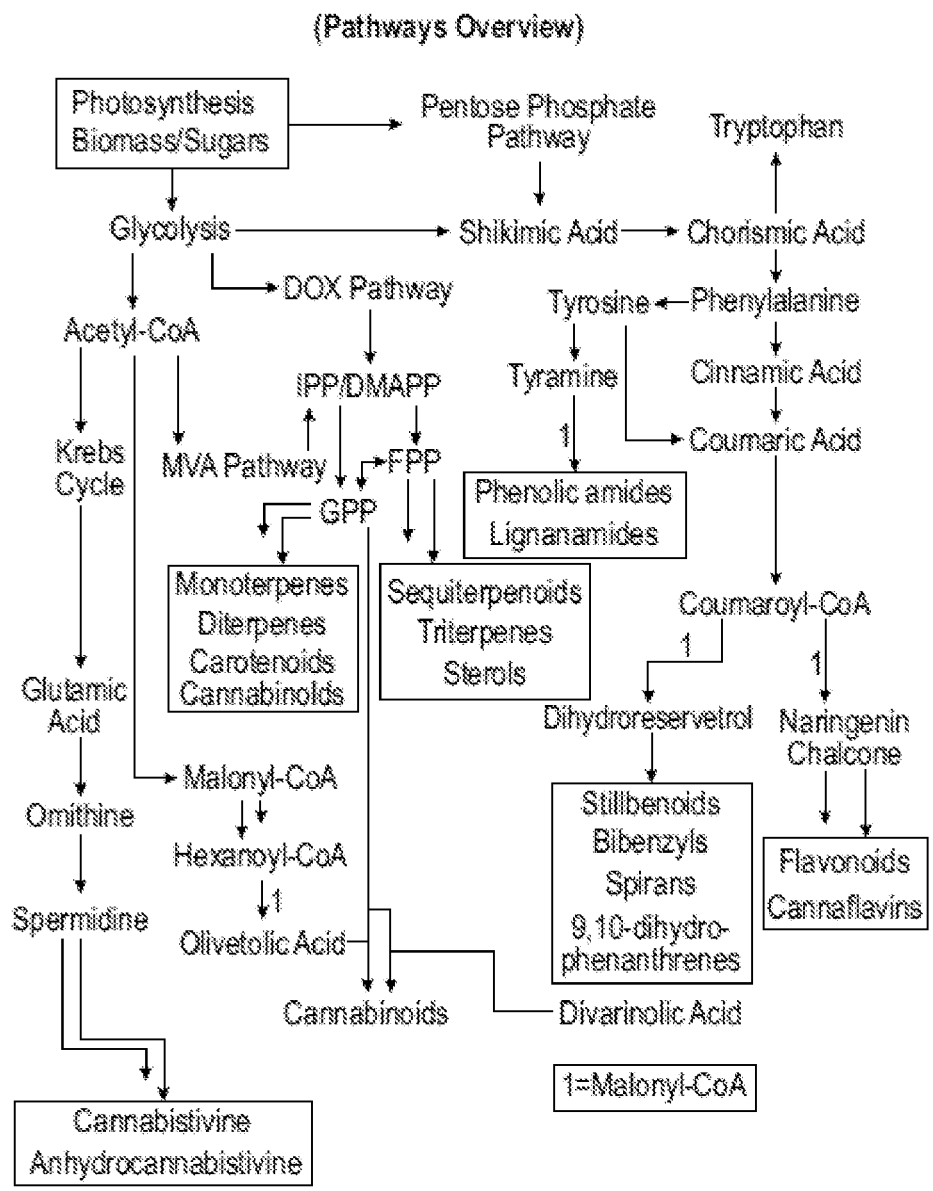
FIG. 7 is a diagram of the combined biosynthetic pathways of FIGS. 1-6.

FIG. 7 is the total pathway overview, showing how all the different classes of compounds can be made, and the general paths they take for being biosynthesized in the cell.

Overview of Procedure

A general scheme of the work flow is as follows:

1) Regular/modified/synthetic gene(s) of select enzymes are processed and inserted into an expression system (vector, cosmid, BAC, YAC, phage, etc.) to produce modified hosts.

2) Mod host is then optimized for efficient production and yield via manipulation, silencing, and amplifying inserted or other genes in the host, leading to an efficient system for product. It is important to remember that every organism is different, and to get a specific compound each optimization will also be different.

3) Mod host can produce enzymes and final products/intermediates, or be further modified using host engineering techniques. (Host engineering Can also be performed before insertion of exp. System)

4) Mod and engineering hosts produce products and intermediates.

5) Product is purified and can be further modified/processed.

In Table 1, different final products are listed along with possible uses. This list is by no means exhaustive, and as such this patent covers any molecules that are made this way. Table 2 lists all possible starting materials that can be utilized for a cheap and efficient biosynthesis.

In more detail, referring to the inter-conversion of sugars, we employ enzymes readily available in the market. Pure enzyme stock can be diluted and added to a solution with the substrates. Once the reaction is complete, we can filter out the enzyme via dialysis tubing, by precipitation out of the solution, chromatography, or other industrial methods for filtration and purification. Each step in FIGS. 1 to 7 will give work with this strategy, leading us up to the final products or key intermediate molecules. Certain steps in the process can be worked on by using chemical and physical methods as well. For example, prenylation of certain compounds can be done outside the cell, as it may be advantageous to do so since unprenylated compounds are also high value compounds. Small batches can be prenylated accordingly to demand via a chemical process.

There are also commercially available cell free expression systems, which are able to produce proteins without the need of any host. With appropriate optimization steps, it is possible to get a cheap and efficient process for production of these compounds using identified starting molecules.

Application Techniques

Referring to bacterial, yeast, plant, and algae incorporation of genes, there are a number of strategies that can be applied to achieve this. We can:

1) Add genes for 1-10 enzymes in various commercially available vectors, cosmids, plasmids, etc. Only need 1-10 enzymes added, as others are already built in most living organisms. For example, glycolysis pathway and related enzymes are already present in most hosts.

2) Bioengineer genes for better yield and suitability in the host.

3) Bioengineer strains of bacteria and yeast that are specialized in producing important molecules. Many metabolic strategies exist, with identification by appropriate screening methods:

1) Rational metabolic engineering: engineering pathways using available information 2) Evolutionary engineering: using random genetic perturbations and/or mutations (via random mutagenesis in whole genome and/or parts)

3) Transposon mutagenesis & gene overexpression libraries: overexpression and/or deletion of single or multiple genes;

4) Global transcription machinery engineering: basal transcription factors mutagenesis causing a global reprogramming of gene transcription and/or translation One strategy is to suppress any pathway that is not essential to our goals or the survival of the host. Another is to enhance our key pathways, or mixing and matching the two methods. The second strategy is through rapid directed evolution, possible by producing many generations so eventually we get a generation of host that has evolved with our genes/functions of interest.

4) Bioengineer custom basic life forms that are specifically making our products, using another organism or using synthetic/modifications. Components from other hosts and system to make a custom organism.

5) Bioengineer bacteria and yeast to have enzyme genes in their chromosomes, and make intermediates or final products inside the host. The product of this process can further be modified.

6) Propagate various colonies of organisms which co-exist symbiotically, with the first making our starting material after utilizing a precursor, and the other colonies making our final product. This process can also be incorporated into an ecosystem type setup of different chambers, each holding different organisms that use specific parts of the raw material to produce intermediates or final products that can be modified post-manufacturing.

Referring to the extraction of enzymes once they have been produced in the host, there are many ways to isolate and purify our enzymes. Many organisms have the ability to excrete proteins, which can be collected much easier than cell lysis, as known by those skilled in the art. This technique is the preferred method.

Another method is to lyse the host culture and purify with traditional biochemistry methods (gels, centrifugation, ammonium sulfate precipitation, etc.), use a specialized nickel column with a prep HPLC (need to add a HIS tag to our proteins; remove HIS tag after purification), etc.

Example 1 (Bacterial)

Bacteria (*E. coli*, etc.) are inserted with exp. system giving us a modified host. The mod host can either be further processed or it can generate products. Products/intermediates are made in the host, and may be either enzymes that are further extracted and used in vitro, or we add substrates into the bacterial culture so they use the enzymes produced in them to make the substrate. Either way (protein or prod production), purification is carried out to get final products, or intermediates that can be further processed in vitro to give final products. Throughout this procedure, host engineering can be carried out at any step of any process to get better yields.

Example 2 (Plants)

Plant tissue can be used as a starting material to get a tissue culture going. Appropriate expression vectors/systems carry our interest genes into the cells. Alternatively, cell engineering can lead to many combinations that may have similar or different outcomes. The culture can be grown into full plants, and products are ingested by consuming the plants (e.g. tomatoes with certain cannabinoids produced within, etc.). The second way uses the cell culture in a synthetic environment to produce final products/intermediates. Finally, product is purified and used.

Example 3 (Algae)

Algae are modified with the usual techniques used for host engineering. Once completed, the mod host can be embedded into a system similar to biofuel production from algae. Using sunlight and some nutrients, the algae produces final products/intermediates, which is appropriately filtered from the bulk. Other products generated can be further processed to get biofuels or other important compounds that can readily be sold in the market.

Example 4 (Fungi)

Fungi modified with the techniques can:
1) Use plastic to produce final products/intermediates. Plastic needs to be processed and broken down into components before being used in this process via chemical and biological processes, known by those skilled in the art.
2) Clean up waste, whilst producing final products/intermediates at the same time.
3) Produce beer and wine with fungi that also makes final prod/intermediates. Beer and wine will contain our compounds of interest.
4) Use fungi cultures to produce compounds of interest.
5) Genes for s. cerevisiae strains to be modified for better yields of final products:
    tHMGR
    upc2-1 (allows higher uptake of exogenous sterol fivefold from medium)
    ERG genes (ERG6, ERG2, ERG3, ERG1, ERG11, ERG24, ERG25, ERG9, ERG10, ERG13, ERG12, ERGS, ERG19, ERG20)
    HMGR1 and HMGR2
    IDI genes
    Gal80p
    DPP1, ADH2, and ALD6 genes
    FPP/GPP synthase (chose avian FPP synthase as it exhibits higher catalytic turnover rates and lower Kms for substrates than other prenyltransferases)

Figure 8:
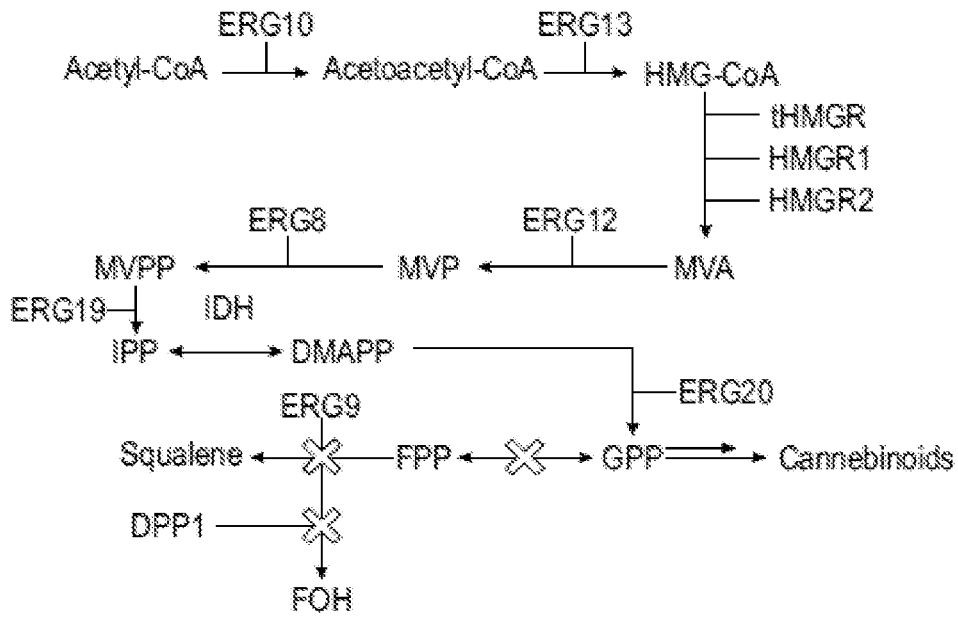
FIG. 8 is diagram of the genetic modification of certain genes for higher product yield in *Saccharomyces cerevisiae* yeast.
Figure 8:
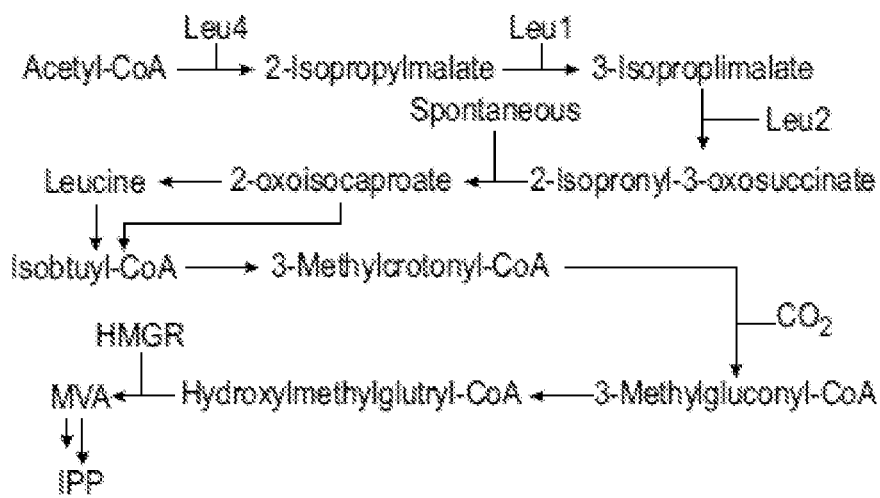

Manipulation, deletion, overexpression, and other modifications to the genes listed above will produce strains that are highly efficient for the production of our compounds of interest. These strains have an exogenous sterol uptake, as the internal sterol pathway has been disabled by manipulations so that all the carbon flux can be directed toward the production of our compounds of interest. Example of genetic pathway regulation in yeast is shown in FIG. 8.

Our initial strategy in *s. cerevisiae* was to increase the carbon flux of our pathways of interest, while decreasing or eliminating pathways that led carbon flux away from our pathways as well. We also focused on exogenous sterol uptake for higher production and secretion levels, cell permeability for more efficient and cheaper production, along with focusing the pathways on utilizing the cheapest sugars. Dynamic control over ergosterol regulation can increase yields as well. Overall result is a strain that is has increased yield many fold, while making the overall production more stable and cheaper.

1) Perform EMS mutagenesis on yeast strains (BY4741, BY4742, CEN.PK, CEN.PK2, EPY300) to get colonies with a SUE (sterol uptake exogenous) mutation. This enables us to provide exogenous sterol to the yeast while cancelling out the gene that diverts carbon flux towards ergosterol, thereby increasing total carbon flux. Without the SUE mutation, the cell diverts lots of carbon flux toward manufacturing sterols, thereby diverting the pools of intermediates away from our compounds and interest leading to very low yields.

2) Perform ERG1 and ERG9 gene knockouts. ERG1 knockout stops the activity of conversion of squalene to squalene epoxide, thereby complementing the SUE mutation and allowing higher uptake of exogenous ergosterol, while ERG9 knockout takes out the cells ability to divert carbon flux towards other metabolites.

3) On some lines, we can perform a DPP1 knockout. DPP1 knockout ensures that isoprenoids farnesyl pyrophosphate (FPP) and GPP are not converted to FOH, thereby blocking the pathway towards FOH products in the cell.

4) Perform ERG2, ERG3, or ERG6 mutations in different cell lines, while performing upregulation mutation on upc2-1 gene (general transcription factor) on all three lines. This helps increase cell membrane permeability for better excretion of our compounds without the need for cell lysis and having the ability to use two-phase or continuous fermentation. This also allows the cells to uptake more fatty acids, thereby increasing the yield many fold.

5) Overexpression of ERG10, ERG13, HMGR1/2 or tHMGR, ERG12, ERGS, IDI1, HFA1 genes in yeast inserted via vectors. By overexpression of these genes, we are amplifying the enzymes of the MVA pathway from the sugars to our compounds, thereby amplifying the intermediates and final products.

6) Modification of avian and/or *salmonella* ERG20 gene encoded FPP synthase (ERG20p). Some cells lines can also be modified using the Erg20p(F96C) mutations. This allows for higher Kms and increased catalytic turnover compared to endogenous GPP synthase, while the engineering itself allows for production of GPP.

7) Gal80p gene deletion so we do not need to use galactose sugar when inducing promoter expression. This is important since others have used galactose promoters, which need expensive galactose sugars for production. By deleting this gene, the cells bypass the need for galactose to express enzymes, leading to cheaper and more efficient biosynthesis.

8) Adding ADH2p promoter to induce strong transcription under conditions with low glucose. This promoter is more efficient than the GAL promoter, and has best results while using non-glucose sugars (ethanol, fructose, etc.) which are cheaper.

9) On some lines, we also overexpress ADH2 and ALD6 genes, along with overexpression of an acetyl-CoA C-acetyltransferase to increase efficiency of the system, while also gaining the ability to convert ethanol to acetate efficiently.

10) Adding and overexpressing enzymes for the production of CBDA (OS-OAC fusion enzyme, CsPti, CBDA Synthase), constructed in a single vector. These enzymes are codon optimized.

11) Grow colonies while adding free fatty acids, and hexanoic acid (for THCA, CBDA, CBGA, CBCA) or butyric acid (for THCVA, CBDVA, CBGVA, CBCVA).

12) For production of THCA/THCVA, use THCA synthase in step 10 instead of CBDA synthase. For production of CBGA/CBGVA, follow step 10 but don't use CBDA synthase in vector construct. For production of CBCA/CBCVA, use CBC synthase in step 10 instead.

Our strategy for *Pichia pastoris* (*Pichia* Pink 1, 2, 3 from Invitrogen) yeast was similar to *S. Cerevisiae*, except for the following differences:
1) Each enzyme, vector, and primer were optimized for insertion into *pichia* cells instead of *S. cerevisiae*.

2) Methanol is used to supplement cells in addition to free fatty acid, hexanoic acid, and butyric acid, thereby reducing the total cost of production many fold, while eliminating any contamination issues from other species.

3) No EMS mutagenesis is performed.

4) Knockouts of pep4 (encoding Proteinase A), prb1 (encoding Proteinase B), and YPS1 genes are also introduced. These knockouts allow for the integration of high copy plasmids leading to higher yields.

5) Steps 7, 8, and 9 from the *S. cerevisiae* strategy above are not to be performed in *pichia* cells.

Example 5 (Cell Free Expression Systems)

Vectors are introduced into cell free expression systems, and make either enzymes or intermediate/final products. Further processing or steps are needed to get purified final products.

Procedures

EMS Mutagenesis (S. Cere.; BY4741, BY4742, CEN. PK, CEN. PK2, BY300)

1) Cells incubated overnight @ 30 C in 5 mL TPD medium while shaking @200 rpm to establish 200 mL YPD shake flask culture.

2) When OD600 of yeast culture reaches 1.0, cells are spun down by centrifugation (12 mins at 4,000 g), washed twice with 20 mL 0.1M sodium phosphate buffer, pH7.0.

3) Cells concentrated by centrifugation again, re-suspended in 1 mL 0.1M sodium phosphate buffer, transferred to 30 mL FALCON tubes, treated with 300 uL EMS (1.2 g/mL).

4) Cells are incubated at 30 C for 1 hr while shaking.

5) Stop mutagenesis by adding 8 mL of sterile 5% sodium thiosulfate to yeast cells.

6) Cells are pelleted, washed with 8 mL sterile water, concentrated by centrifugation, re-suspended in 1 mL sterile water and 100 uL aliquots plated into YPD-NCS agar plate (YPD+50 mg/L each of cholesterol, nystatin, sqalestatin, and 2% Bacto-agar).

7) In some instances, washed cells were resuspended in 1 mL YPDE liquid media for overnight recovery before plating to YPD-NCS agar medium.

8) Incubate cultures for up to two weeks at 30 C until distinct colonies are visible.

Bacteria & Yeast Culturing

1) Grown using standard culture practices.

2) YPD media without selection consisted of 1% Bacto-yeast extract, 2% Bacto-peptone, and 2% glucose.

3) Add 40 mg/L ergosterol to YPD media to get YPDE media.

4) Add 40 mg/L each of nystatin, cholesterol, and squalestatin to YPD media to get TPDNCS media.

5) Add 40 mg/L each of ergosterol and squalestatin to YPD media to get YPDSE media.

6) Prepare minimal media, SCE (pH5.3), by adding 0.67% Bacto-yeast nitrogen base (without amino acids), 2% dextrose, 0.6% succinic acid, 0.14% Sigma yeast dropout soln (-his, -leu, -ura, -trp), uracil (300 mg/L), L-tryptophan (150 mg/L), L-histidine (250 mg/L), L-methionine (200 mg/L), L-leucine (1 g/L), and 40 mg/L of ergosterol.

7) Cholesterol and ergosterol stocks are 10 mg/mL in 50% Triton X-100, 50% ethanol and kept at −20 C.

8) Selection media prepared similarly except without supplementation of media with indicated reagent based on the yeast auxotrophic markers.

9) All solid media plates are prepared with 2% Bacto-agar.

Yeast Transformation & Culture Performance

1) Used FROZEN-EZ Yeast Transformation II Kit from Zymo Research, Orange, Calif, according to manufacturer's recommendations.

2) 1 ug of plasmid was used per transformation, followed by selection on agar plates of SCE medium lacking specified amino acids for auxotrophic markers, or YPDE containing 300 mg/L hygromycin B for screening erg9 knockout at 30 C.

3) Colonies are picked and used to start 3 mL cultures in minimal media to characterize their terpene production capabilities. (6 days incubation at 30 C while shaking)

4) Best cultures are chosen to move further, using 30 mL shake flask cultures.

5) Cultures are grown to saturation in minimal media, inoculated into 30 mL SCE media and 1 mL aliquots are taken out daily for 15 days.

6) Cell growth is monitored via change in optical density at 600 nm every two days using dilutions at later stages of growth.

7) Production of terpenes is determined via testing.

ERG9 Knockout Mutations

1) Primers ERG9PS1 and ERG9-250downS2 used to amplify hygromycin resistance gene, hphNT1, from the pFA6-hph-NT1 vector.

2) Simulataneously add 42 bp nucleotide sequences homologous to regions surrounding ERG9 gene in yeast genome.

3) Purified PCR fragment is transformed into various cell lines identified in phase 2 with the ability to accumulate farnesol and selected on YPDE plates containing 300 mg/L hygromycin.

4) Independent single colonies are picked for ergosterol dependent test, PCR confirmation of recombination with hphF and ERG9 450DWR primer.

5) Farnesol production analysis done by GC-MS/LC-MS.

ERG1 Knockot Mutations

1) Primers ERG1F and ERG1R used to amplify the sqalene epoxidase synthase ERG1 gene by using Takara high fidelity Primerstar taq polymerase.

2) Obtained PCR fragment is gel purified, A tailed and ligated into the pGEM-Teasy vector.

3) Obtained vector is used as template to run second PCR with primers Erg1-splitF and EGR1-splitR to obtain PCR fragment with deletion of 891 bp CDS in the middle, yet containing 310 bp at 5' end region and 291 bp at 3' end region of ERG1 gene which are the target homologous recombination sequence for ERG1 knockout.

4) After digestion with BamHI, self-ligation, and transformation to DH5alpha competent cells, resulting vector is pGEM-ERG1-split.

5) Padh-Kanmx4-Tcyc-LoxP antibiotic selection marker cassette is constructed by assembly PCR of three fragments.

6) Padh promoter is PCR amplified with Padh-loxP-ManHIF and Padh-Kanmx4R primers using Yep352 vector as a template.

7) Kanmx4 selection gene is PCR amplified using Padh-kanmx4F and Tcyc-kanmx4R primers using PYM-N14 plasmid as a template.

8) Tcyc terminator was PCR amplified with Padh-loxP-BamHIF and Padh-Kanmx4R primers using Pesc vector as a template.

9) 3 PCR fragments containing homologous regions with each other were gel purified and 250 ng of each fragment were mixed together to serve as template for the secondary assembly PCR reaction to yield pAdh-Kanmx4-Tcyc-LoxP cassette.

10) Cassette is digested and inserted into pGEM-ERG1-split vector, and used as template to run PCR with ERG1F and ERG1R to get PCR fragment used to generate cell lines.

11) Pgpd-tHMGR-Tadh fragment was amplified from Pesc-Gpd-leu-tHMGR vector with primers GPD-BamHIP and Tadh-XholIR.

12) Insert fragment into pGEM-ERG1-split vector containing kanmx4 cassette.

13) Use construct as template to amplify with ERG1F and EGR1R primers to gain the fragment for building slightly different cell lines, which include integration of one copy of tHMGR into the ERG1 gene.

| Primer Name | Primer Sequence |
| --- | --- |
| ERG9pS1 (SEQ ID NO: 1) | TACATTTCATAGCCCATCTTCAACAACAATACCGACTTACCCGTACGCTGCAGGTCGAC |
| ERG9 250dwS2 (SEQ ID NO: 2) | CAGATTGACGGAGAGAGGGCCACATTGTTTGTCGGCAATAAATCGATGAATTCGAGCTCG |
| Hph F (SEQ ID NO: 3) | ATGGGTAAAAAGCCTGAACTCA |
| Hph R (SEQ ID NO: 4) | TTATTCCTTTGCCCTCGGACGAG |
| ERG9 450dwR (SEQ ID NO: 5) | AGATGCTAGTCAATGGCAGAAG |
| ERG9p300upF (SEQ ID NO: 6) | TGCTTACACAGAGTGAACCTGC |
| ERG9 300R (SEQ ID NO: 7) | CTCGTGGAAGTGACGCAAC |
| pGPD-BamHI F (SEQ ID NO: 8) | cgGGATCCagtttatcattatcaatactcgcc |
| pGPD-NotIR (SEQ ID NO: 9) | gggGCGGCCGCgagctcagtdatcattatc |
| tHMGR-NotIF (SEQ ID NO: 10) | GGGGCGGCCGCAAAACAATGTTGTCACGACTTTTCCGTATGC |
| tHMGR-SpeIR (SEQ ID NO: 11) | GACTAGT TCAAGCTGACTTCTTGGTGCACGTTCCTTG |
| ERG1F (SEQ ID NO: 12) | ATGTCTGCTGTTAACGTTGCACCTG |
| ERG1R (SEQ ID NO: 13) | TTAACCAATCAACTCACCAAAC |
| ERG1-split F (SEQ ID NO: 14) | CGGGATCCCTCGAG TTGTTCGCTGCTGACAGCGATAAC |
| ERG1-splitR (SEQ ID NO: 15) | CGGGATCCGCTAGCGGTACCACATGGGTCCTTTATATTGACACG |
| ERG1 90up F (SEQ ID NO: 16) | ATCAGAACAATTGTCCAGTATTG |
| ERG1100dwR (SEQ ID NO: 17) | AATGTACTATACAAGCCTTCC |
| bSQS-NotIF (SEQ ID NO: 18) | GGGGCGGCCGCAAAACAATGGGGATGCTTCGCTGGGGAGT |
| bSQS-SpeIR (SEQ ID NO: 19) | GACTAGTTTAGCTCCTCAATTCGTCAAAGGT |
| Cre-NotIF (SEQ ID NO: 20) | GGGGCGGCCGCAAAACAATGGACATGTTCAGGGATCGCCAGG |
| Cre-SpeIR (SEQ ID NO: 21) | GACTAGTCTAATCGCCATCTTCCAGCAGGCG |
| Padh-Loxp-BamHIF (SEQ ID NO: 22) | CGGGATCCATAACTTCGTATAGCATACATTATACGAAGTTATGTGGAATATTTCGGATAT |
| Padh-Kanmx4F (SEQ ID NO: 23) | GCATACAATCAACTAAGCTAAGCTAAAACAATGGGTAAGGAAAAGACTCACGTTTC |
| Padh-Kanmx4R (SEQ ID NO: 24) | GAAACGTGAGTCTTTTCCTTACCCATTGTTTTAGCTTAGCTTAGTTGATTGTATGC |

| Primer Name | Primer Sequence |
|---|---|
| Kanmx4-TcycF (SEQ ID NO: 25) | CATTTGATGCTCGATGAGTTTTTCTAAATCCGCTCTAACCGAAAAGGAAGGAG |
| Kanmx4-TcycR (SEQ ID NO: 26) | CTCCTTTCCTTTTCGGTTAGAGCGGATTTAGAAAAACTCATCGAGCATCAAATG |
| Tcyc-LoxP-NheIR (SEQ ID NO: 27) | GGGGCTAGCATAACTTCGTATAATGTATGCTATACGAAGTTATCTTCGAGCGTCCCAAA |
| Gpd-BamHIF (SEQ ID NO: 28) | CGGGATCCAGTTTATCATTATCAATACTCG |
| Tadh-XhoIR (SEQ ID NO: 29) | GGGCTCGAGGAGCGACCTCATGCTATACCTG |
| Kanmx4R (SEQ ID NO: 30) | TTAGAAAAACTCATCGAGCATC |

Expression of Enzymes for Cannabinoid Production

LS 5'FWD
SEQ ID NO: 31
Length: 55
Type: DNA
Organism: Artificial Sequence
Notes: Primer

```
caccagaacttagtttcgacggataaa
atggaaaccggtttgtcctcggtttgcac
```

All REV
SEQ ID NO: 33
Length: 58
Type: DNA
Organism: Artificial Sequence
Notes: Primer

```
Gcatagaatctaatctaagtttaaa
atgaatcatttgagagcagaagggcctgc
```

CB 5' FWD
SEQ ID NO: 32
Length: 56
Type: DNA
Organism: Artificial Sequence
Notes: Primer

```
cataactaattacatgatttaaccTTAAACATCAGATTCAATAGAGCCGC
CTCCACTG
```

Backbone |CBGA synthase |Flexible spacer |CBD synthase target peptide
SEQ ID NO: 31
Length:
Type: DNA
Organism: artificial sequence
Notes: Codon optimized

```
  1 ggttaaatca tgtaattagt tatgtcacgc ttacattcac gccctccccc cacatccgct
 61 ctaaccgaaa aggaaggagt tagacaacct gaagtctagg tccctattta ttttttata
121 gttatgttag tattaagaac gttatttata tttcaaattt ttcttttttt tctgtacaga
181 cgcgtgtacg catgtaacat tatactgaaa accttgcttg agaaggtttt gggacgctcg
241 aaggctttaa tttgcggccc ctcacctgca cgcaaaatag gataattata ctctatttct
301 caacaagtaa ttggttgttt ggccgagcgg tctaaggcgc ctgattcaag aaatatcttg
361 accgcagtta actgtgggaa tactcaggta tcgtaagatg caagagttcg aatctcttag
421 caaccattat ttttttcctc aacataacga gaacacacag gggcgctatc gcacagaatc
481 aaattcgatg actggaaatt ttttgttaat ttcagaggtc gcctgacgca tatacctttt
541 tcaactgaaa aattgggaga aaaaggaaag gtgagagcgc cggaaccggc ttttcatata
601 gaatagagaa gcgttcatga ctaaatgctt gcatcacaat acttgaagtt gacaatatta
661 tttaaggacc tattgttttt tccaataggt ggttagcaat cgtcttactt tctaactttt
721 cttacctttt acatttcagc aatatatata tatatatttc aaggatatac cattctaatg
781 tctgccccta agaagatcgt cgttttgcca ggtgaccacg ttggtcaaga aatcacagcc
```

-continued

```
 841 gaagccatta aggttcttaa agctatttct gatgttcgtt ccaatgtcaa gttcgatttc
 901 gaaaatcatt taattggtgg tgctgctatc gatgctacag gtgttccact tccagatgag
 961 gcgctggaag cctccaagaa ggctgatgcc gttttgttag gtgctgtggg tggtcctaaa
1021 tggggtaccg gtagtgttag acctgaacaa ggtttactaa aaatccgtaa agaacttcaa
1081 ttgtacgcca acttaagacc atgtaacttt gcatccgact ctcttttaga cttatctcca
1141 atcaagccac aatttgctaa aggtactgac ttcgttgttg tcagagaatt agtgggaggt
1201 atttactttg gtaagagaaa ggaagatgat ggtgatggtg tcgcttggga tagtgaacaa
1261 tacaccgttc cagaagtgca aagaatcaca agaatggccg ctttcatggc cctacaacat
1321 gagccaccat tgcctatttg gtccttggat aaagctaatg ttttggcctc ttcaagatta
1381 tggagaaaaa ctgtggagga aaccatcaag aacgaattcc ctacattgaa ggttcaacat
1441 caattgattg attctgccgc catgatccta gttaagaacc caacccacct aaatggtatt
1501 ataatcacca gcaacatgtt tggtgatatc atctccgatg aagcctccgt tatcccaggt
1561 tccttgggtt tgttgccatc tgcgtccttg gcctctttgc cagacaagaa caccgcattt
1621 ggtttgtacg aaccatgcca cggttctgct ccagatttgc caaagaataa ggtcaaccct
1681 atcgccacta tcttgtctgc tgcaatgatg ttgaaattgt cattgaactt gcctgaagaa
1741 ggtaaggcca ttgaagatgc agttaaaaag gttttggatg caggcatcag aactggtgat
1801 ttaggtggtt ccaacagtac caccgaagtc ggtgatgctg tcgccgaaga agttaagaaa
1861 atccttgctt aaaaagattc tcttttttta tgatatttgt acataaactt tataaatgaa
1921 attcataata gaaacgacac gaaattacaa aatggaatat gttcataggg taacgctatg
1981 atccaatatc aaaggaaatg atagcattga aggatgagac taatccaatt gaggagtggc
2041 agcatataga acagctaaag ggtagtgctg aaggaagcat acgatacccc gcatggaatg
2101 ggataatatc acaggaggta ctagactacc tttcatccta cataaataga cgcatataag
2161 tacgcattta agcataaaca cgcactatgc cgttcttctc atgtatatat atatacaggc
2221 aacacgcaga tataggtgcg acgtgaacag tgagctgtat gtgcgcagct cgcgttgcat
2281 tttcggaagc gctcgttttc ggaaacgctt tgaagttcct attccgaagt tcctattctc
2341 tagaaagtat aggaacttca gagcgctttt gaaaaccaaa agcgctctga agtcgcactt
2401 tcaaaaaacc aaaaacgcac cggactgtaa cgagctacta aatattgcg aataccgctt
2461 ccacaaacat tgctcaaaag tatctctttg ctatatatct ctgtgctata tccctatata
2521 acctaccat ccacctttcg ctccttgaac ttgcatctaa actcgacctc tacatttttt
2581 atgtttatct ctagtattac tctttagaca aaaaaattgt agtaagaact attcatagag
2641 tgaatcgaaa acaatacgaa aatgtaaaca tttcctatac gtagtatata gagacaaaat
2701 agaagaaacc gttcataatt ttctgaccaa tgaagaatca tcaacgctat cactttctgt
2761 tcacaaagta tgcgcaatcc acatcggtat agaatataat cggggatgcc tttatcttga
2821 aaaaatgcac ccgcagcttc gctagtaatc agtaaacgcg ggaagtggag tcaggctttt
2881 tttatggaag agaaaataga caccaaagta gccttcttct aaccttaacg gacctacagt
2941 gcaaaagtt atcaagagac tgcattatag agcgcacaaa ggagaaaaaa agtaatctaa
3001 gatgctttgt tagaaaaata gcgctctcgg gatgcatttt tgtagaacaa aaagaagta
3061 tagattcttt gttggtaaaa tagcgctctc gcgttgcatt tctgttctgt aaaatgcag
3121 ctcagattct tgtttgaaa aattagcgct ctcgcgttgc attttgtttt tacaaaaatg
3181 aagcacagat tcttcgttgg taaatagcg ctttcgcgtt gcatttctgt tctgtaaaaa
3241 tgcagctcag attcttgtt tgaaaaatta gcgctctcgc gttgcatttt tgttctacaa
```

-continued

```
3301  aatgaagcac agatgcttcg ttcaggtggc acttttcggg gaaatgtgcg cggaacccct
3361  atttgtttat ttttctaaat acattcaaat atgtatccgc tcatgagaca ataaccctga
3421  tattggtcag aattggttaa ttggttgtaa cactgacccc tatttgttta ttttctaaa
3481  tacattcaaa tatgtatccg ctcatgagac ataaccctg ataaatgctt caataatatt
3541  gaaaaggaa gaatatgagc catattcaac gggaaacgtc gaggccgcga ttaaattcca
3601  acatggatgc tgatttatat gggtataaat gggctcgcga taatgtcggg caatcaggtg
3661  cgacaatcta tcgcttgtat gggaagcccg atgcgccaga gttgtttctg aaacatggca
3721  aaggtagcgt tgccaatgat gttacagatg agatggtcag actaaactgg ctgacggaat
3781  ttatgccact ccgaccatc aagcattta tccgtactcc tgatgatgca tggttactca
3841  ccactgcgat ccccggaaaa acagcgttcc aggtattaga agaatatcct gattcaggtg
3901  aaaatattgt tgatgcgctg gcagtgttcc tgcgccggtt gcactcgatt cctgtttgta
3961  attgtccttt taacagcgat cgcgtatttc gcctcgctca ggcgcaatca cgaatgaata
4021  acggtttggt tgatgcgagt gattttgatg acgagcgtaa tggctggcct gttgaacaag
4081  tctggaaaga aatgcataaa cttttgccat ctcaccgga ttcagtcgtc actcatggtg
4141  atttctcact tgataaccct attttgacg aggggaaatt aataggttgt attgatgttg
4201  gacgagtcgg aatcgcagac cgataccagg atcttgccat cctatggaac tgcctcggtg
4261  agttttctcc ttcattacag aaacggcttt ttcaaaaata tggtattgat aatcctgata
4321  tgaataaatt gcaatttcat ttgatgctcg atgagttttt ctaactcatg accaaaatcc
4381  cttaacgtga gttacgcgcg cgtcgttcca ctgagcgtca gaccccgtag aaaagatcaa
4441  aggatcttct tgagatcctt ttttctgcg cgtaatctgc tgcttgcaaa caaaaaaacc
4501  accgctacca gcggtggttt gtttgccgga tcaagagcta ccaactcttt ttccgaaggt
4561  aactggcttc agcagagcgc agataccaaa tactgttctt ctagtgtagc cgtagttagc
4621  ccaccacttc aagaactctg tagcaccgcc tacatacctc gctctgctaa tcctgttacc
4681  agtggctgct gccagtggcg ataagtcgtg tcttaccggg ttggactcaa gacgatagtt
4741  accggataag gcgcagcggt cgggctgaac ggggggttcg tgcacacagc ccagcttgga
4801  gcgaacgacc tacaccgaac tgagatacct acagcgtgag ctatgagaaa gcgccacgct
4861  tcccgaaggg agaaaggcgg acaggtatcc ggtaagcggc agggtcggaa caggagagcg
4921  cacgagggag cttccagggg gaaacgcctg gtatctttat agtcctgtcg gtttcgcca
4981  cctctgactt gagcgtcgat ttttgtgatg ctcgtcaggg gggcggagcc tatggaaaaa
5041  cgccagcaac gcggcctttt tacggttcct ggccttttgc tggccttttg ctcacatgtt
5101  ctttcctgcg ttatccctg attctgtgga taaccgtatt accgcctttg agtgagctga
5161  taccgctcgg ggtcgtgcag gtagtttatc attatcaata ctcgccattt caaagaatac
5221  gtaaataatt aatagtagtg attttcctaa ctttatttag tcaaaaaatt agccttttaa
5281  ttctgctgta acccgtacat gcccaaaata gggggcgggt tacacagaat atataacatc
5341  gtaggtgtct gggtgaacag tttattcctg gcatccacta aatataatgg agcccgcttt
5401  ttaagctggc atccagaaaa aaaagaatc ccagcaccaa aatattgttt tcttcaccaa
5461  ccatcagttc ataggtccat tctcttagcg caactacaga gaacagggc acaaacaggc
5521  aaaaaacggg cacaacctca atggagtgat gcaaccagcc tggagtaaat gatgacacaa
5561  ggcaattgac ccacgcatgt atctatctca ttttcttaca ccttctatta ccttctgctc
5641  tctctgattt ggaaaaagct gaaaaaaaag gttgaaacca gttccctgaa attattcccc
```

-continued

```
5701 tacttgacta ataagtatat aaagacggta ggtattgatt gtaattctgt aaatctattt
5761 cttaaacttc ttaaattcta cttttatagt tagtcttttt tttagtttta aaacaccaga
5821 acttagtttc gacggataaa atggaaaccg gtttgtcctc ggtttgcact ttctccttcc
5881 aaacaaacta tcatacactc ctgaacccgc acaataacaa tcccaaaact tccctgctgt
5941 gttataggca cccaaagaca ccaatcaaat actcctacaa taactttcca tctaagcatt
6001 gtagcacaaa aagtttccat ttgcaaaata agtgttccga atctctgtcc atcgccaaaa
6061 attccattag ggctgccact actaatcaaa ctgaaccacc agagtctgat aatcattctg
6121 tcgccacaaa gattctgaat tttgggaagg cttgttgaa gttacaaaga ccatatacaa
6161 ttattgcctt tacctcttgt gcctgtggtt tatttggtaa ggaactgttg cataatacaa
6241 atttaatatc ttggtcattg atggaaacgt tcaaagcatt ttttttctta gtcgctatcc
6301 tttgtattgc ttctttcacc accactatca accagattta cgacttacat attgacagaa
6361 ttaacaagcc agatttgcca ctggcttcgg gcgagatttc cgtcaatact gcctggatca
6421 tggaaacttc tattattgtt gccttgtttg gattgataat caccataaaa atggaaacta
6481 agggtggtcc attgtatatt ttcggttact gttttggtat cttcggggc atcgtctact
6541 ctgttcctcc attcagatga aaacaaaatc cttccacagc attccttttg aacttcctgg
6601 cgcacattat aaccaacttt acttttttatt atgcctccag agccgccctg gggctgccct
6661 ttgaattacg cccctccttt acattttac tggccttcat ggagaccaag tccatggaga
6721 ctggttctgc tctcgcgttg atcaaagatg cttccgatgt ggaaggtgac accaaatttg
6761 gtatatccac tttggccagc aagtatggtt ccaggaattt gaccctattt tgttctggta
6841 tcgtgctgct gtcttatgtt gcagccatct tggctggcat catttggcca caggcttca
6901 attcaaatgt tatggagacg ctgctctcgc atgctatttt ggcattttgg ttgattctac
6961 agacaagaga ttttgcttta accaattatg acccagaagc tggtagaaga ttttacgaat
7021 ttatggaaac atggaaatta tactatgctg aatatttagt gtacgttttc attgggggcg
7081 gctccagcgc cggcggcggc tcttctgcgg gcggttggtc tcatccacaa tttgagaaag
7141 gtgggtcgtc tggcggcggc agcggggggcg ggtccggcgg ggggagcggc ggtatgaaat
7201 gttcgaccttc ctcttttttgg tttgtctgta aaataatttt ttttttcttc agctttaaca
7261 ttcaaaccag cattgcaaat ccaagagaaa atttcttgaa atgcttttca caatatatcc
7321 ccaataatgc tactaacttg aagctagttt atactcaaaa caacccttttg tacatgtccg
7361 tgctcaactc caccattcac aacctaagat tcacttcaga cactacccca aaaccattag
7441 ttattgtgac accttctcac gtttcacata tccaaggtac tattttatgc tccaagaagg
7501 tcggcctgca aattagaact agatctggag gtcatgattc agaaggaatg tcttacatct
7561 ctcaagttcc atttgtgatt gtcgatttaa gaaatatgag gagcattaag atcgatgttc
7621 actcccaaac ggcatgggtt gaagccggtg ccaccttggg cgaagtttac tactgggtca
7681 acgagaagaa tgaaaactta tcactagccg caggttattg tccaactgtt tgtgctggtg
7741 gccatttcgg aggcggcggc tacggtcctc taatgagaaa ctacggctta gctgctgaca
7801 atatcatcga cgctcacttg gttaacgttc atggtaaagt tttagataga aaatctatgg
7861 gtgaggatct tttctgggct ttgagaggtg gcggcgcaga atcatttggc attatcgttg
7921 cttggaagat cagattggtg gctgtcccca agtctacaat gttttctgtg aagaaaatta
7961 tggaaatcca tgaattggtc aaactggtga ataaatggca aaacatagct tacaagtacg
8041 ataaagactt gctgttaatg acacatttta ttaccaggaa catcactgat aaccaaggca
8101 agaacaagac tgcaattcat acttattttt cctccgtttt tttgggtggt gtcgactccc
```

-continued

```
8161  tcgtggatct gatgaataaa tcattccctg aactaggtat taaaaaaacc gattgtagac
8221  aattgagttg gattgatacc atcatattct acagtggtgt tgttaattat gatactgaca
8281  acttcaacaa agaaatactg ctggaccgtt ccgccggcca gaatggtgct tttaaaatca
8341  agttggatta tgtgaaaaag cctattccag aatccgtatt tgttcaaata ttggaaaagc
8401  tgtatgaaga agacattggt gcaggcatgt acgctcttta tccttatggc ggcataatgg
8461  atgaaatttc tgaaagtgcc attcctttcc cacatagggc cgggatcctg tacgagttat
8521  ggtacatttg ttcatgggaa aagcaagaag ataatgaaaa acatttaaat tggataagaa
8561  atatttataa ttttatgact ccatacgtct ccaaaaaccc acgcctggca tatttgaatt
8641  acagagacct ggatattggc atcaatgatc ctaaaaaccc aaataattac actcaggcaa
8701  gaatatgggg tgaaaaatat ttcggcaaaa attttgatag gctggtcaag gttaaaacac
8761  tggttgatcc aaacaatttc tttagaaacg aacaatctat cccacctctg cctagacata
8821  gacacggcgg tggaagcagt ggaggcggct ctattgaatc tgatgtttaa tga
```

Backbone |OLS |Flexible spacer |OAC |target peptide
SEQ ID NO: 35
Length: 25
Type: DNA
Organism: artificial sequence
Notes: Codon optimized

```
   1  ggttaaatca tgtaattagt tatgtcacgc ttacattcac gccctccccc cacatccgct
  61  ctaaccgaaa aggaaggagt tagacaacct gaagtctagg tccctattta ttttttata
 121  gttatgttag tattaagaac gttatttata tttcaaattt ttcttttttt tctgtacaga
 181  cgcgtgtacg catgtaacat tatactgaaa accttgcttg agaaggtttt gggacgctcg
 241  aaggctttaa tttgcggccc ctcacctgca cgcaaaaagc ttttcaattc aattcatcat
 301  ttttttttta ttcttttttt tgatttcggt ttctttgaaa ttttttttgat tcggtaatct
 361  ccgaacagaa ggaagaacga aggaaggagc acagacttag attggtatat atacgcatat
 421  gtagtgttga agaaacatga aattgcccag tattcttaac ccaactgcac agaacaaaaa
 481  ccagcaggaa acgaagataa atcatgtcga aagctacata taaggaacgt gctgctactc
 541  atcctagtcc tgttgctgcc aagctatttta atatcatgca cgaaaagcaa acaaacttgt
 601  gtgcttcatt ggatgttcgt accaccaagg aattactgga gttagttgaa gcattaggtc
 661  ccaaaatttg tttactaaaa acacatgtgg atatcttgac tgatttttcc atggagggca
 721  cagttaagcc gctaaaggca ttatccgcca agtacaattt tttactattc gaagatagaa
 781  aatttgctga cattggtaat acagtcaaat tgcagtactc tgcgggtgta tacagaatag
 841  cagaatgggc agacattacg aatgcacacg gtgtggtggg cccaggtatt gttagcggtt
 901  tgaagcaggc ggcagaagaa gtaacaaagg aacctagagg cctttttgatg ttagcagaat
 961  tgtcatgcaa gggctcccta tctactggag aatatactaa gggtactgtt gacattgcga
1021  aaagcgacaa agattttgtt atcggcttta ttgctcaaag agacatgggt ggaagagatg
1081  aaggttacga ttggttgatt atgacacccg gtgtgggttt agatgacaag ggagatgcat
1141  tgggtcaaca gtatagaacc gtgatgatg ttgtctctac aggatctgac attattattg
1201  ttggaagagg actatttgca aagggaaggg atgctaaggt agagggtgaa cgttacagaa
2161  aagcaggctg gaagcatat tgagaagat gcggccagca aaactaaaaa actgtattat
1321  aagtaaatgc atgtatacta aactcacaaa ttagagcttc aatttaatta tatcagttat
```

-continued

```
1381  tacccacgct atgatccaat atcaaaggaa atgatagcat tgaaggatga gactaatcca
1441  attgaggagt ggcagcatat agaacagcta aagggtagtc ctgaaggaag catacgatac
1501  cccgcatgga atgggataat atcacaggag gtactagact acctttcatc ctacataaat
1561  agacgcatat aagtacgcat ttaagcataa acacgcacta tgccgttctt ctcatgtata
1621  tatatataca ggcaacacgc agatataggt gcgacgtgaa cagtgagctg tatgtgcgca
1681  gctcgcgttg cattttcgga agcgctcgtt ttcggaaacg ctttgaagtt cctattccga
1741  agttcctatt ctctagaaag tataggaact tcagagcgct tttgaaaacc aaaagcgctc
1801  tgaagtcgca cttttcaaaaa accaaaaacg caccggactg taacgagcta ctaaaatatt
1861  gcgaataccg cctccacaaa cattgctcaa aagtatctct ttgctatata tctctgtgct
1921  atatccctat ataacctacc catccaccct tcgctccttg aacttgcatc taaactcgac
1981  ctctacattt tttatgttta tctctagtat tactctttag acaaaaaaat tgtagtaaga
2041  actattcata gagtgaatcg aaaacaatac gaaaatgtaa acatttccta tacgtagtat
2101  atagagacaa aatagaagaa accgttcata attttctgac caatgaagaa tcatcaacgc
2161  tatcactttc tgttcacaaa gtatgcgcaa tccacatcgg tatagaatat aatcggggat
2221  gcctttatct tgaaaaaatg cacccgcagc ttcgctagta atcagtaaac gcgggaagtg
2281  gagtcaggct ttttttatgg aagagaaaat agacaccaaa gtagccttct tctaacctta
2341  acggacctac agtgcaaaaa gttatcaaga gactgcatta tagagcgcac aaaggagaaa
2401  aaaagtaatc taagatgctt tgttagaaaa atagcgctct cgggatgcat ttttgtagaa
2461  caaaaaagaa gtatagattc tttgttggta aaatagcgct ctcgcgttgc atttctgttc
2521  tgtaaaaatg cagctcagat tctttgtttg aaaaattagc gctctcgcgt tgcattttttg
2581  ttttacaaaa atgaagcaca gattcttcgt tggtaaaata gcgatttcgc gttgcatttc
2641  tgttctgtaa aaatgcagct cagattcttt gtttgaaaaa ttagcgctct cgcgttgcat
2701  ttttgttcta caaaatgaag cacagatgct tcgttcaggt ggcactttttc ggggaaatgt
2761  gcgcggaacc cctatttgtt tattttttcta aatacattca aatatgtatc cgctcatgag
2821  acaataaccc tgatattggt cagaattggt taattggttg taacactgac ccctattttgt
2881  ttattttttct aaatacattc aaatatgtat ccgctcatga gacaataacc ctgataaatg
2941  cttcaataat attgaaaaag gaagaatatg agtattcaac atttccgtgt cgcccttatt
3001  cccttttttg cggcatttttg ccttcctgtt tttgctcacc cagaaacgct ggtgaaagta
3061  aaagatgctg aagatcagtt gggtgcacga gtgggttaca tcgaactgga tctcaacagc
3121  ggtaagatcc ttgagagttt tcgccccgaa gaacgttttc caatgatgag cacttttaaa
3181  gttctgctat gtggcgcggt attatcccgt attgacgccg ggcaagagca actcggtcgc
3241  cgcatacact attctcagaa tgacttggtt gagtactcac cagtcacaga aaagcatctt
3301  acggatggca tgacagtaag agaattatgc agtgctgcca taaccatgag tgataacact
3361  gcggccaact tacttctgac aacgatcgga ggaccgaagg agctaaccgc ttttttgcac
3421  aacatggggg atcatgtaac tcgccttgat cgttgggaac cggagctgaa tgaagccata
3481  ccaaacgacg agcgtgacac cacgatgcct gtagcgatgg caacaacgtt gcgcaaacta
3541  ttaactggcg aactacttac tctagcttcc cggcaacaat taatagactg gatggaggcg
3601  gataaagttg caggaccact tctgcgctcg gcccttccgg ctggctggtt tattgctgat
3661  aaatccggag ccggtgagcg tggttctcgc ggtatcatcg cagcgctggg gccagatggt
3721  aagccctccc gtatcgtagt tatctacacg acggggagtc aggcaactat ggatgaacga
3781  aatagacaga tcgctgagat aggtgcctca ctgattaagc attggtaact catgaccaaa
```

-continued

```
3841  atcccttaac gtgagttacg cgcgcgtcgt tccactgagc gtcagacccc gtagaaaaga
3901  tcaaaggatc ttcttgagat cctttttttc tgcgcgtaat ctgctgcttg caaacaaaaa
3961  aaccaccgct accagcggtg gtttgtttgc cggatcaaga gctaccaact cttttttccga
4021  aggtaactgg cttcagcaga gcgcagatac caaatactgt tcttctagtg tagccgtagt
4081  tagcccacca cttcaagaac tctgtagcac cgcctacata cctcgctctg ctaatcctgt
4141  taccagtggc tgctgccagt ggcgataagt cgtgtcttac cgggttggac tcaagacgat
4201  agttaccgga taaggcgcag cggtcgggct gaacggggggt tcgtgcaca cagcccagct
4261  tggagcgaac gacctacacc gaactgagat acctacagcg tgagctatga gaaagcgcca
4321  cgcttcccga agggagaaag gcggacaggt atccggtaag cggcagggtc ggaacaggag
4381  agcgcacgag ggagcttcca gggggaaacg cctggtatct ttatagtcct gtcgggtttc
4441  gccacctctg acttgagcgt cgatttttgt gatgctcgtc aggggggcgg agcctatgga
4501  aaaacgccag caacgcggcc ttttttacggt tcctggcctt ttgctggcct tttgctcaca
4561  tgttcttttcc tgcgttatcc cctgattctg tggataaccg tattaccgcc tttgagtgag
4621  ctgataccgc tcggggtcgt gcaggtatag cttcaaaatg tttctactcc tatttactc
4681  ttccagattt tctcggactc cgcgcatcgc cgtaccactt caaaacaccc aagcacagca
4741  tactaaattt cccctctttc ttcctctagg gtgtcgttaa ttacccgtac taaaggtttg
4801  gaaaagaaaa aagtgaccgc ctcgtttctt tttcttcgtc gaaaaggca ataaaaattt
4861  ttatcacgtt tcttttctt gaaaattatt ttttttgatt ttttctctt tcgatgacct
4921  cccattgata tttaagttaa taaacggact tcaatttctc aagtttcagt ttcatttttc
4981  ttgttctatt acaactttt ttacttcttg ctcattagaa agaaagcata gcaatctaat
5041  ctaagtttaa aatgaatcat ttgagagcag aagggcctgc ttccgtgctg gctattggta
5101  ccgccaatcc agaaaatatc ctgctgcagg acgaattccc agattactat tttagggtca
5161  ccaaatctga acatatgaca caattgaaag agaaattcag aaagatttgt gacaagtcca
5221  tgattaggaa aagaaattgt tttttgaatg aagaacactt gaagcaaaat cctcgcctgg
5281  tggagcatga aatgcaaact ttgatgcta gacaagacat gttggtggtg gaagttccaa
5341  agctggggaa ggatgcctgt gccaaggcca ttaaagaatg gggccaacca aaatccaaaa
5401  ttacccacct gatttttcacc tccgcctcca ccactgatat gccaggtgca gactatcatt
5461  gtgctaaatt gttgggtttg tcccctccg tgaagagagt tatgatgtat caattaggtt
5521  gttatggcgg cggcaccgtt ctgagaattg ccaaagacat tgctgaaaac aataaaggtg
5581  cgcgcgtttt ggctgtttgt tgtgatatta tggcatgttt atttagaggt ccaagtgaaa
5641  gtgacttgga attgctagtg ggccaggcca tatttggtga tggtgccgct gctgtgatcg
5701  ttggtgctgc gcctgatgaa tctgtcggtg aaagaccaat ttttgaactg gtttccactg
5761  gtcaaaccat tttgccaaat tcagaaggta ctattggcgg ccatatcaga gaagctggtt
5821  taatctttga tttgcacaag gatgtcccaa tgttaatttc caataatatt gaaaaatgtt
5881  tgatcgaagc atttaccccc atcggtattt ctgattggaa ttccatcttc tggattacac
5941  atcctggcgg taaagctatc ttagataaag ttgaggagaa gttgcattta aagtctgaca
6001  aatttgttga ttcaagacat gtcctgtctg agcacggtaa tatgtcttcc tcgaccgtct
6061  tgtttgtcat ggatgagttg aggaagaggt ccctggaaga aggcaagagc accaccggtg
6121  acggttttga gtgggggtc ctctttggat ttgggccagg cctgaccgta gaaagggttg
6181  ttgtccgctc ggtgccaatc aaatatggtg gggggtccag cgccggtggc gggagctccg
```

-continued

```
6241 cgggcggttg gtctcaccca caatttgaaa agggtggcag cagcggcggc ggctctggcg 6301 gaggctccgg cgggggctcg gggggtatgg ctgtcaagca tctgatcgtg ctgaagttca 6361 aagatgaaat tactgaagcc caaaaggagg aatttttcaa gacatatgtt aatttggtta 6421 acatcattcc agcaatgaaa gatgtttatt ggggtaagga cgttactcaa aaaaataagg 6481 aagagggtta cactcatatt gttgaagtca ctttcgaatc cgtcgaaaca attcaagatt 6541 atattattca tccagctcat gttgggtttg gcgatgtgta cagatcattt tgggaaaaat 6601 tattgatttt tgactacaca ccaagaaaag gcggtggaag cagtggaggc ggctctattg 6661 aatctgatgt ttaatag
```

Overexpression of ERG8m HFA1, ERG 10, ERG13, tHMGR, HMGR, ERG12, ERG8, IDI Genes (for higher levels of intermediates)

Same process as expression of Synthase expression, but with 3 copies expressed in yeast cells.

Backbone |GGPS1|2a protease |HMC-CoA reductase- |flexible spacer IDI|

SEQ ID NO: 36
Length:
Type: DNA
Organism: artificial sequence
Notes: Codon optimized

```
   1 atggagaaga ctcaagaaac agtccaaaga attcttctag aaccctataa atacttactt 61 cagttaccag gtaaacaagt gagaaccaaa ctttcacagg catttaatca ttggctgaaa 121 gttccagagg acaagctaca gattattatt gaagtgacag aaatgttgca taatgccagt 181 ttactcatcg atgatattga agacaactca aaactccgac gtggctttcc agtggcccac 241 agcatctatg gaatcccatc tgtcatcaat tctgccaatt acgtgtattt ccttggcttg 301 gagaaagtct aacccttga tcacccagat gcagtgaagc tttttacccg ccagcttttg 361 gaactccatc agggacaagg cctagatatt tactggaggg ataattacac ttgtcccact 421 gaagaagaat ataaagctat ggtgctgcag aaaacaggtg gactgtttgg attagcagta 481 ggtctcatgc agttgttctc tgattacaaa gaagatttaa aaccgctact taatacactt 541 gggctctttt tccaaattag ggatgattat gctaatctac actccaaaga atatagtgaa 601 aacaaaagtt tttgtgaaga tctgacagag ggaaagttct catttcctac tattcatgct 661 atttggtcaa ggcctgaaag cacccaggtg cagaatatct tgcgccagag aacagaaaac 721 atagatataa aaaaatactg tgtacattat cttgaggatg taggttcttt tgaatacact 781 cgtaataccc ttaaagagct tgaagctaaa gcctataaac agattgatgc acgtggtggg 841 aaccctgagc tagtagcctt agtaaaacac ttaagtaaga tgttcaaaga agaaaatgaa 901 ggcggttctg gcagcggaga gggcagagga agtcttctaa catgcggtga cgtggaggag 961 aatcccggcc ctaggtctgg cagcgagag ggcagaggaa gtcttctaac atgcggtgac 1021 gtggaggaga atcccggccc taggacacaa aagaaagtcc cagacaattg ttgtagacgt 1081 gaacctatgc tggtcagaaa taaccagaaa tgtgattcag tagaggaaga gacagggata 1141 aaccgagaaa gaaaagttga ggttataaaa cccttagtgg ctgaaacaga taccccaaac 1201 agagctacat tgtggttgg taactcctcc ttactcgata cttcatcagt actggtgaca 1261 caggaacctg aaattgaact tccagggaa cctcggccta tgaagaatg tctacagata 1321 cttgggaatg cagagaaagg tgcaaaattc cttagtgatg ctgagatcat ccagttagtc 1381 aatgctaagc atatcccagc ctacaagttg gaaactctga tggaaactca tgagcgtggt
```

-continued

```
1441  gtatctattc gccgacagtt actttccaag aagctttcag aaccttcttc tctccagtac 1501  ctaccttaca gggattataa ttactccttg gtgatgggag cttgttgtga aatgttatt 1561  ggatatatgc ccatccctgt tggagtggca ggacccttt gcttagatga aaaagaattt 1621  caggttccaa tggcaacaac agaaggttgt cttgtggcca gcaccaatag aggctgcaga 1681  gcaataggtc ttggtggagg tgccagcagc cgagtccttg cagatgggat gactcgtggc 1741  ccagttgtgc gtcttccacg tgcttgtgac tctgcagaag tgaaagcctg gctcgaaaca 1801  tctgaagggt tcgcagtgat aaaggaggca tttgacagca ctagcagatt tgcacgtcta 1861  cagaaacttc atacaagtat agctggacgc aacctttata tccgtttcca gtccaggtca 1921  ggggatgcca tggggatgaa catgatttca aagggtacag agaaagcact ttcaaaactt 1981  cacgagtatt tccctgaaat gcagattcta gccgttagtg gtaactattg tactgacaag 2041  aaacctgctg ctataaattg gatagaggga agaggaaaat ctgttgtttg tgaagctgtc 2101  attccagcca aggttgtcag agaagtatta aagactacca cagaggctat gattgaggtc 2161  aacattaaca gaatttagt gggctctgcc atggctggga cataggagg ctacaacgcc 2221  catgcagcaa acattgtcac cgccatctac attgcctgtg acaggatgc agcacagaat 2281  gttggtagtt caaactgtat tactttaatg gaagcaagtg gtcccacaaa tgaagattta 2341  tatatcagct gcaccatgcc atctatagag ataggaacgg tgggtggtgg gaccaaccta 2401  ctacctcagc aagcctgttt gcagatgcta ggtgttcaag gagcatgcaa agataatcct 2461  ggggaaaatg cccggcagct tgcccgaatt gtgtgtggga ccgtaatggc tggggaattg 2521  tcacttatgg cagcattggc agcaggacat cttgtcaaaa gtcacatgat tcacaacagg 2581  tcgaagatca atttacaaga cctccaagga gcttgcacca agaagacagc cggctcagga 2641  ggttcttcag gactggaagt gctgtttcag ggcccgggtg gatctggcat gatgcctgaa 2701  ataaacacta accacctcga caagcaacag gttcaactcc tggcagagat gtgtatcctt 2761  attgatgaaa atgacaataa aattggagct gagaccaaga agaattgtca cctgaacgag 2821  aacattgaga aaggattatt gcatcgagct tttagtgtct tcttattcaa caccgaaaat 2881  aagcttctgc tacagcaaag atcagatgct aagattacct ttccaggttg ttttacgaat 2941  acgtgttgta gtcatccatt aagcaatcca gccgagcttg aggaaagtga cgcccttgga 3001  gtgaggcgag cagcacagag acggctgaaa gctgagctag gaattcccctt ggaagaggtt 3061  cctccagaag aaattaatta tttaacacga attcactaca agctcagtc tgatggtatc 3121  tggggtgaac atgaaattga ttacatttg ttggtgagga agaatgtaac tttgaatcca 3181  gatcccaatg agattaaaag ctattgttat gtgtcaaagg aagaactaaa agaacttctg 3241  aaaaaagcag ccagtggtga aattaagata acgccatggt ttaaaattat tgcagcgact 3301  tttctcttta aatggtggga taacttaaat catttgaatc agtttgttga ccatgagaaa 3361  atatacagaa tg
```

TABLE 1

| Compounds | Pharmacological Chararactoistics |
|---|---|
| Cannabinoids (FIG. 1 and 2) | |
| Cannabigerolic acid (CBGA) | Antibiotic (1) |
| Cannabigerolic acid monomethylether (CBGAM) | |
| Cannabigerol (CBG) | Antibiotic, antifungal. anti-inflammatory, analgesic (1) Partial agonist at CB1/CB2 receptors (2) |
| Cannabigerovarinic acid (CBGVA) | |
| Cannabigerovarin (CBGV) | |
| Cannabichromenic acid. (CBCA) | |
| Caimabichromene (CBC) | Anti-inflammatory, antibiotic, antifungal, analgesic (1) |
| Cannabichromevarinic acid (CBCVA) | |
| Cannabichromevarin (CBCV) | |
| Cannabidiolic acid. (CBDA) | Antibiotic |
| Cannabidiol (CBD) | Anxiolytic antipsychotic, analgesic, anti-inflammatory, antioxidant, antispasmodic (1) Ant schizophrenic, antiepileptic, sleep-promoting, anti-oxidizing, anti-inflammatory, immunomodulation properties (2) |
| Cannabidiol monomethylether (CBDM) | |
| Cannabidiol-C4 (CBD-C4) | |
| Cannabidivarinic acid (CBDVA) | |
| Cannabidivarin (CBDV) | |
| Cannabidiorcol (CBD-C1) | |
| Tetrahydrocannabinolic acid A (THCA-A) | |
| Tetrahydrocannabinolic acid B (THCA-B) | |
| Delta-9-tetrahydrocannabinol (THC) | Euphoriant, analgesic, anti-inflammatory, antioxidant, antiemetic (1) |
| Delta-9-tetrahydrocannabinolic acid-C4 (THCA-C4) | |
| Delta-9-tetrahydrocannabinol-C4 (THC-C4) | |
| Delta-8-tetrahydrocaanabivarin (D8-THCV) | Exhibit in vitro pharm properties similar to THCV, and both can antagonize THC; behave as agonists or antagonists in dose dependent manner (2) |
| Delta-9-tetrahydrocannabivarinic acid (THCVA) | |
| Delta-9-tetrahydrocannabivarin (THCV) | Analgesic, euphoriant (1) Strong antagonist of anandamide (due to interactions with non-CB1/2 receptors), neuromodulator (in animal and human organs), some affects due to interaction with non CB1/CB2 receptors (2) |
| Delta-9-tetrahydrocannabiorcolic acid (THCA-C1) | |
| Delta-9-tetrahydrocannabiorcol (THC-C1) | |
| Delta-7-cis-iso-tetrahydrocannabivarin (D7-THCV) | |
| Delta-8-tetrahydrocannabinolic acid (D8-THCA) | |
| Delta-8-tetrahydrocannabinol (D8-THC) | Similar to THC (1) Several 1-O-methyl- and 1-deoxy-delta-8-THC analogs have high CB2 receptor affinity [JWH133 JWH359, trans-(6aR, 10aR)-3 -(1,1-dimethylhexyl)-1-O-methyl-delta-8-THC]; antiemetic effects similar to THC (2) |
| Cannabicyclolic acid (CBLA) | |
| Cannabicyclol (CBL) | |
| Cannabicyclovarin (CBLV) | |
| Cannabielsoic acid A (CBEA-A) | |
| Cannabielsoic acid B (CBEA-B) | |
| Cannabielsoin (CBE) | |
| Cannabinolic acid (CBNA) | |
| Cannabinol (CBN) | Sedative, antibiotic, anticonvulsant, anti-inflammatory (1) |
| Cannabinol methylether (CBNM) | |
| Cannabinol-C4 (CBN-C4) | |
| Cannabivarin (CBV) | |
| Cannabinol-C2 (CBN-C2) | |
| Cannabinol-C1 (CBN-C1) | |
| Cannabinodiol (CBND) | |
| Cannabinodivarin (CBVD) | |
| Cannabitriol (CBT) | |
| 10-Ethoxy-9-hydroxy-delta-6a-tetrahydrocannabinol | |
| 8,9-Dihydroxy-delta-6a-tetrahydrocannabinol | |
| Cannabitriolvarin (CBTV) | |
| Ethoxy-cannabitriolvarin (CBTVE) | |
| Dehydrocannabifuran (DCBF) | |
| Cannabifuran (CBF) | |
| Cannabichromanon (CBCN) | |
| Cannabicitran(CBT) | |
| 10-oxo-delta-6a-tetrahydrocannabinol (OTHC) | |
| Delta-9-cis-tetrahydrocannabinol (Cis-THC) | |

TABLE 1-continued

| Compounds | Pharmacological Chararactoistics |
|---|---|
| 3,4,5,6-Tetrahydro-7-hydroxy-alpha-alpha-2-trimethyl-9-n-propyl-2,6-methano-2H-1-benzoxocin-5-methanol (OH-iso-HHCV) | |
| Cannabiripsol (CBR) | |
| Trihydroxy-delta-9-tetrahydrocannabinol (triOH-THC) | |
| Terpenes/Terpenoids | |
| Beta-Myrcene | Analgesic. anti-inflammatory, antibiotic, antimutagenic |
| d-Limonene | Immune potentiator, antidepressant, antimutagenic |
| Linalool | Sedative. antidepressant, anxiolytic, immune potentiator |
| Trans-Ocimene | |
| Beta-Pinene | |
| Alpha-Pinene | Anti-inflammatory, bronchodilator stimulant, antibiotic, antineoplastic. AChE inhibitor |
| Beta-Caryophyllene | Anti-inflammatory, cytoprotective, antimalarial, CB2 agonist |
| Delta-3-Carene | |
| Pulegone | AChE inhibitor, sedative, antipyretic |
| Trans-gamma-Bisabolene | |
| Trans-alpha-Farnesene | |
| Beta-Fenchol | |
| Beta-Phellandrene | |
| Alpha-Humulene | |
| Guajol | |
| Alpha-Gualene | |
| Alpha-Eudesmol | |
| Terpinolene | |
| Alpha-Selinene | |
| Alpha-Terpineol | Sedative, antibiotic, AChE inhibitor, antioxidant, antimalarial |
| Fenchone | |
| Camphene | |
| Cis-Sabinene hydrate | |
| Cis-Ocimene | |
| Beta-Eudesmol | |
| Beta-Selinene | |
| Alpha-trans-Bergamolene | |
| Gamma-Eudesmol | |
| Borneol | |
| Cis-beta-Farnescene | |
| Gamma-Curcumene | |
| Cis-gamma-Bisabolene | |
| Alpha-Thujene | |
| Epi-alpha-Bisabolol | |
| Ipsdienol | |
| Alpha-Yiangene | |
| Beta-Elemene | |
| Alpha-cis-Bergamontene | |
| Gamma-Muurolene | |
| Alpha-Cadinene | |
| Alpha-Longipinene | |
| Caryophyllene oxide | |
| Spermidine Alkaloids (FIG. 6) | |
| (+)-Cannabisativine | |
| Palustridine | |
| Palustrine | |
| Spermidine | |
| Anhydrocannabisativine | |
| Phenolic Amides and Lignanamides (FIG. 5) | |
| N-trans-Feruloyltyramine | |
| N-p-Coumaroyltyramine | |
| N-trans-Caffeoyltyramine | |
| Grossamide | |
| Cannabisin-A | |
| Cannabisin-B | |
| Cannabisin-C | |
| Cannabisin-D | |
| Cannabisin-E | |
| Cannabisin-F | |
| Cannabisin-G | |
| Phenylpropanoids and Flavonoids (FIG. 4) | |
| Apigenin | |
| Luteolin | |
| Kaempferol | |
| Quercetin | |
| Orientin | |
| Vitexin | |
| Cannflavin A | Inhibit prostaglandin E2 in human rheumatoid synovial cells |
| Cannflavin B | Inhibit prostaglandin E2 in human rheumatoid synovial cells |
| Stilbenoids (FIG. 3) | |
| Cannabispiran | |
| Isocannabispiran | |
| Cannabistilbene-IIa | |
| Cannabistilbene-IIb | |
| Cannithrene-1 | |
| Cannithrene-2 | |
| Acetyl cannabispirol | |
| Alpha-cannabisporanol | |
| Canniprene | |
| Cannabispirone | |

TABLE 2

(Starting Materials)

| | | |
|---|---|---|
| Sugar based concentrates (High Fructose Corn Syrup, Molasses) | Hemicellulose | Glycerol |
| Glucose | Xylose | Whey |
| Sucrose | Methanol | Biodiesel |
| Cellulose | Lactic Acid | Citrate |
| Ethanol | Lignin | Fructose |
| Succinic Acid | Arabinose | Biofuels |
| Biomass | Saccharose | Starch base products |
| Agricultural residue | Water hyacinth | Aquatic biomass |

What is claimed is:

1. An isolated nucleic acid molecule comprising a nucleotide sequence that is at least 95% identical to the nucleic acid sequence set forth in SEQ ID NO: 36, wherein the isolated nucleic acid molecule: (i) is non-naturally occurring; (ii) has a nucleotide sequence that is codon-optimized for expression in a host organism; and (iii) produces at least one cannabinoid precursor selected from the group consisting of isopentenyl pyrophosphate (IPP), geranyl diphosphate (GPP) and farnesyl pyrophosphate (FPP) in the host organism when inserted and expressed in the host organism, and wherein the host organism is *Escherichia coli, Saccharomyces cerevisiae* or *Pichia pastoris*.

2. A host organism that comprises an isolated nucleic acid molecule comprising a nucleotide sequence that is at least 95% identical to the nucleic acid sequence set forth in SEQ ID NO: 36, wherein the isolated nucleic acid molecule: (i) is non-naturally occurring; (ii) has a nucleotide sequence that is codon-optimized for expression in the host organism; and (iii) produces at least one cannabinoid precursor selected from the group consisting of isopentenyl pyrophosphate (IPP), geranyl diphosphate (GPP) and farnesyl pyrophosphate (FPP) in the host organism when inserted and expressed in the host organism, and wherein the host organism is a bacterium, plant alga or fungus.

3. The host organism of claim 2, wherein the host organism is a *Escherichia coli, Saccharomyces cerevisiae* or *Pichia pastoris*.

4. The isolated nucleic acid molecule of claim 1, comprising the nucleic acid sequence set forth in SEQ ID NO: 36.

* * * * *